(12) United States Patent
Bracken et al.

(10) Patent No.: US 8,394,067 B2
(45) Date of Patent: Mar. 12, 2013

(54) MEDICAL DEVICE SECUREMENT SYSTEM

(75) Inventors: Ronald L. Bracken, Monroe, GA (US);
Vasu Nishtala, Snellville, GA (US);
Robert Young, Loganville, GA (US)

(73) Assignee: C.R. Bard, Inc., Covington, GA (US)

( * ) Notice: Subject to any disclaimer, the term of this patent is extended or adjusted under 35 U.S.C. 154(b) by 804 days.

(21) Appl. No.: 12/470,434

(22) Filed: May 21, 2009

(65) Prior Publication Data

US 2010/0298778 A1    Nov. 25, 2010

(51) Int. Cl.
*A61M 25/02* (2006.01)

(52) U.S. Cl. ........................................ 604/180

(58) Field of Classification Search .......... 604/174–180, 604/358, 307, 308, 386, 391, 392, 393; 428/447
See application file for complete search history.

(56) References Cited

U.S. PATENT DOCUMENTS

| | | | |
|---|---|---|---|
| 3,167,072 A | 1/1965 | Stone et al. | |
| 3,700,574 A * | 10/1972 | Kehr ............................... | 522/23 |
| 3,834,380 A | 9/1974 | Boyd | |
| 3,993,081 A | 11/1976 | Cussell | |
| 4,059,105 A * | 11/1977 | Cutruzzula et al. ........... | 604/180 |
| 4,082,094 A | 4/1978 | Dailey | |
| 4,114,618 A | 9/1978 | Vargas | |
| 4,129,128 A | 12/1978 | McFarlane | |
| 4,161,177 A | 7/1979 | Fuchs | |
| 4,170,995 A | 10/1979 | Levine et al. | |
| 4,224,937 A | 9/1980 | Gordon | |
| 4,250,880 A | 2/1981 | Gordon | |
| 4,333,468 A | 6/1982 | Geist | |
| 4,356,599 A | 11/1982 | Larson et al. | |
| 4,362,156 A | 12/1982 | Feller, Jr. et al. | |
| 4,389,754 A | 6/1983 | Sohma | |
| 4,397,647 A | 8/1983 | Gordon | |
| 4,405,163 A | 9/1983 | Voges et al. | |
| 4,453,933 A | 6/1984 | Speaker | |
| 4,480,639 A | 11/1984 | Peterson et al. | |
| 4,500,338 A * | 2/1985 | Young et al. .................. | 504/151 |
| 4,533,349 A | 8/1985 | Bark | |
| 4,621,029 A * | 11/1986 | Kawaguchi ................... | 428/447 |
| 4,623,102 A | 11/1986 | Hough, Jr. | |

(Continued)

FOREIGN PATENT DOCUMENTS

| | | |
|---|---|---|
| EP | 0 931 560 | 7/1999 |
| JP | 52-4691 | 2/1977 |

(Continued)

OTHER PUBLICATIONS

Search Result, Percufix® Catheter Cuff Kit, downloaded from the Internet on Aug. 15, 2001.

*Primary Examiner* — Kevin C Sirmons
*Assistant Examiner* — Michael J Anderson
(74) *Attorney, Agent, or Firm* — Knobbe Martens Olson & Bear LLP

(57) ABSTRACT

A securement device, system, and method for use with a medical article. The securement device, system, or method may include a body that has a top surface and a bottom surface. The bottom surface has an adhesive compound thereon. A resilient retainer formed from a soft, tacky elastomeric gel or foam is supported by the bottom surface of the body. The resilient retainer receives and secures a medical device. The medical device is secured to the skin of a patient upon affixing the bottom surface to the patient via the adhesive compound.

27 Claims, 20 Drawing Sheets

U.S. PATENT DOCUMENTS

| | | | |
|---|---|---|---|
| 4,636,552 A * | 1/1987 | Gay et al. ..................... 525/63 |
| 4,659,329 A | 4/1987 | Annis |
| 4,711,636 A | 12/1987 | Bierman |
| 4,733,666 A | 3/1988 | Mercer, Jr. |
| 4,775,121 A | 10/1988 | Carty |
| 4,852,844 A | 8/1989 | Villaveces |
| 4,857,058 A | 8/1989 | Payton |
| 4,897,082 A | 1/1990 | Erskine |
| 4,898,587 A | 2/1990 | Mera |
| 4,919,654 A | 4/1990 | Kalt |
| 4,997,421 A | 3/1991 | Palsrok et al. |
| 5,037,397 A | 8/1991 | Kalt et al. |
| 5,084,026 A | 1/1992 | Shapiro |
| 5,098,399 A | 3/1992 | Tollini |
| 5,192,273 A | 3/1993 | Bierman et al. |
| 5,192,274 A | 3/1993 | Bierman |
| 5,226,892 A | 7/1993 | Boswell |
| 5,266,401 A | 11/1993 | Tollini |
| 5,308,337 A | 5/1994 | Bingisser |
| 5,334,186 A | 8/1994 | Alexander |
| 5,336,195 A | 8/1994 | Daneshvar |
| 5,352,211 A | 10/1994 | Merskelly |
| 5,354,282 A | 10/1994 | Bierman |
| 5,382,239 A | 1/1995 | Orr et al. |
| 5,389,082 A | 2/1995 | Baugues et al. |
| 5,413,562 A | 5/1995 | Swauger |
| 5,484,420 A | 1/1996 | Russo |
| 5,494,245 A | 2/1996 | Suzuki et al. |
| 5,499,976 A | 3/1996 | Dalton |
| 5,539,020 A * | 7/1996 | Bracken et al. ............ 523/212 |
| 5,551,421 A | 9/1996 | Noureldin et al. |
| D375,355 S | 11/1996 | Bierman |
| 5,643,217 A | 7/1997 | Dobkin |
| 5,681,290 A | 10/1997 | Alexander |
| 5,685,859 A | 11/1997 | Kornerup |
| D389,911 S | 1/1998 | Bierman |
| 5,776,106 A * | 7/1998 | Matyas ..................... 604/180 |
| 5,800,402 A | 9/1998 | Bierman |
| 5,827,239 A | 10/1998 | Dillon et al. |
| 5,846,255 A | 12/1998 | Casey |
| 5,916,199 A | 6/1999 | Miles |
| 5,922,470 A * | 7/1999 | Bracken et al. ............ 428/447 |
| 5,944,696 A | 8/1999 | Bayless et al. |
| 6,015,119 A | 1/2000 | Starchevich |
| 6,054,523 A * | 4/2000 | Braun et al. ................ 524/503 |
| 6,113,577 A | 9/2000 | Hakky et al. |
| 6,131,575 A * | 10/2000 | Lenker et al. ............... 128/885 |
| 6,132,399 A * | 10/2000 | Shultz ........................ 604/174 |
| 6,206,897 B1 | 3/2001 | Jamiolkowski et al. |
| 6,213,979 B1 | 4/2001 | Bierman |
| 6,228,064 B1 | 5/2001 | Abita et al. |
| 6,258,066 B1 * | 7/2001 | Urich .......................... 604/174 |
| 6,273,873 B1 | 8/2001 | Fleischer |
| 6,283,945 B1 | 9/2001 | Bierman |
| 6,361,523 B1 | 3/2002 | Bierman |
| 6,387,075 B1 | 5/2002 | Stivland et al. |
| 6,387,076 B1 | 5/2002 | Landuyt |
| 6,596,402 B2 * | 7/2003 | Soerens et al. ............. 428/447 |
| 6,703,120 B1 * | 3/2004 | Ko et al. .................... 428/355 R |
| 7,115,321 B2 * | 10/2006 | Soerens et al. ............. 428/500 |
| 2002/0161332 A1 * | 10/2002 | Ramey .................... 604/164.07 |
| 2005/0282977 A1 * | 12/2005 | Stempel et al. ............ 525/477 |
| 2006/0025723 A1 | 2/2006 | Ballarini |
| 2006/0289011 A1 * | 12/2006 | Helsel ...................... 128/207.17 |
| 2007/0032561 A1 | 2/2007 | Lin et al. |
| 2008/0249476 A1 | 10/2008 | Bierman et al. |
| 2010/0298778 A1 * | 11/2010 | Bracken et al. ............ 604/180 |

FOREIGN PATENT DOCUMENTS

| | | |
|---|---|---|
| JP | 63-501477 | 6/1988 |
| JP | 01308572 A | 12/1989 |
| WO | WO 96/10435 | 4/1996 |
| WO | WO 98/53872 | 12/1998 |

* cited by examiner

MEDICAL DEVICE SECUREMENT SYSTEM

BACKGROUND OF THE INVENTION

1. Field of the Invention

The present invention relates to a system for securing medical devices to a patient.

2. Description of the Related Art

Medical patients are often in need of repetitious administering of fluids or medications, or repetitious draining of fluids. It is very common in the medical industry to utilize medical tubing to provide various liquids or solutions to a patient. For example, catheters may be used to direct fluids and/or medications into the bloodstream of the patient, or withdraw fluids from the patient. Often, it is desirable to maintain such catheterization or medical tube insertion over an extended period of time during the treatment of a patient. In some instances, a medical article may be attached to a patient for a lengthy period of time, requiring minimal movement for proper functioning.

It is often advantageous to restrict the movement of the medical tube or article, particularly when the medical article is to be administered to the patient over an extended period of time. A medical article that is not securely attached to the patient may move around, which may cause discomfort or injury to the patient, restrict the administering of fluids or medications or the draining of fluids, cause infection, or become dislodged from the patient unintentionally.

It is common for medical providers to affix the medical article to the patient and to attempt to restrict movement of the medical article by taping the medical article to the patient's skin. Medical articles commonly attached in this way include medical lines, luer locks or other types of connectors. Securing a medical article with tape, however, has certain drawbacks.

Tape used to secure a medical article, for example at an insertion site of the medical article on the patient's skin, can collect contaminants and dirt. Such collection of contaminants and dirt can lead to infection. Normal protocol therefore requires periodic tape changes in order to inhibit germ growth. Periodic tape changes may also be necessary when replacing or repositioning the medical article.

Frequent tape changes lead to other problems: excoriation of the patient's skin and adherence of contaminant's to the medical article. Repeated removal of tape can excoriate the skin and cause discomfort to the patient. Additionally, removal of tape can itself cause undesired motion of the catheter device upon the patient and irritation of the patient's skin. Repeated applications of tape over the medical article can lead to the build up of adhesive residue on the outer surface of the medical article. This residue can result in contaminants adhering to the medical article itself, increasing the likelihood of infection. To add to this, residue buildup on the medical article can make the medical article sticker and more difficult to handle for medical providers.

In addition to these drawbacks, tape also fails to limit medical article motion and, therefore, contributes to motion related complications like phlebitis, infiltration and catheter migration. Consequently, there are many problems with using tape to secure a medical article.

It is desirable to avoid directly taping a medical article to a patient. There is a need to provide a simple, yet effective device for securely holding a medical article in place on a patient's skin, while avoiding aggravating the site at which the medical article is mounted. With the increased concern over rising health care costs, there is also a need for simple and less expensive alternatives to safely securing medical articles. Therefore, a need exists for an improved medical article securement system for use with a patient that overcomes the problems associated with current designs.

SUMMARY OF THE INVENTION

The systems and methods disclosed herein have several features, no single one of which is solely responsible for its desirable attributes. Without limiting the scope as expressed by the claims that follow, its more prominent features will now be discussed briefly.

One aspect of the present invention involves a securement device for a medical device. The securement device includes a body and a resilient retainer. The body has a top surface and a bottom surface, and the bottom surface has an adhesive compound thereon. The resilient retainer is formed from a soft, tacky elastomeric gel or foam and is supported by the body. The resilient retainer is adapted for receiving and securing a medical device, where the medical device is secured to the skin of a patient upon affixing the bottom surface to the patient via the adhesive compound.

Another aspect involves a method of securing a medical device to a patient. The method includes providing a securement device and a resilient retainer for the medical device, where the securement device includes a body having a top surface and a bottom surface, the bottom surface having an adhesive compound thereon. The resilient retainer is formed from a soft, tacky elastomeric gel or foam and is supported by the bottom surface of the body. The resilient retainer is adapted for receiving a medical device. The method further includes locating the medical device on the resilient retainer, and securing the securement device and medical device to the patient with the body via the adhesive compound.

In one form, the foam is formed by curing an organopolysiloxane composition. In another form, the organopolysiloxane composition includes a vinyl-containing high viscosity organopolysiloxane or a blend of high viscosity vinyl-containing organopolysiloxanes, a low viscosity organopolysiloxane or a blend of low viscosity organopolysiloxanes, a reinforcing filler, a platinum catalyst, and a hydrogen containing polysiloxane copolymer.

Yet another aspect involves a securement system. The securement system includes a flexible body member and a tacky gel pad. The flexible body member has a first surface and a second surface located opposite the first surface, and the first surface includes an adhesive configured for attachment to a patient. The tacky gel pad is supported by the flexible body member and is configured to deform when pressed against a medical article, where the gel pad inhibits at least lateral and longitudinal motion of the medical article when the flexible body member is attached to the patient.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

These and other features, aspects, and advantages of the invention disclosed herein are described below with reference to the drawings of several embodiments of the present securement system. The illustrated embodiments are intended to illustrate and not to limit the invention. The drawings contain the following figures.

DETAILED DESCRIPTION OF EMBODIMENTS

Figure 1A:
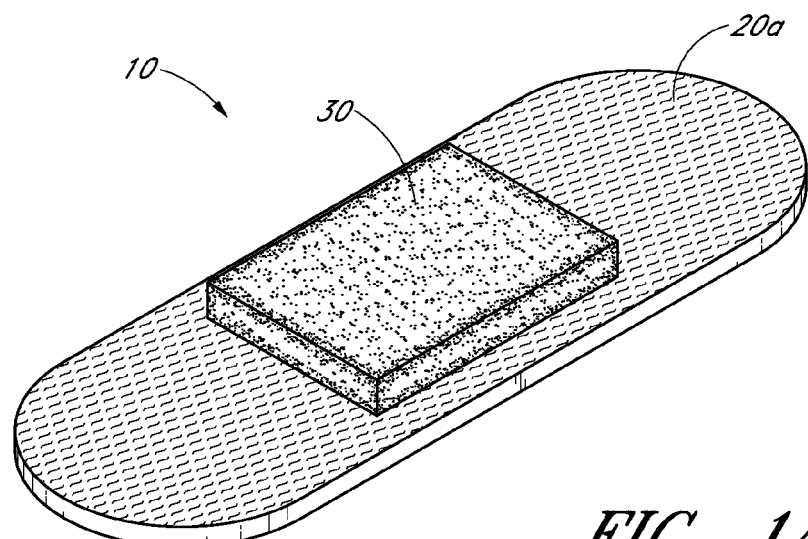
FIG. 1A is a perspective view of a securement device in accordance with a preferred embodiment of the present invention and shows a gel pad.

The following description and examples illustrate embodiments of the present securement system in detail in the context of use with several exemplary medical articles. The principles of the present invention, however, are not limited to the illustrated medical articles. It will be understood by those of skill in the art in view of the present disclosure that the securement system described can be used with any number of articles and medical devices, including, but not limited to: catheters, connector fittings, catheter hubs, catheter adaptors, fluid delivery tubes, and other medical devices or their components, and electrical wires and cables connected to external or implanted electronic devices or sensors. One skilled in the art may also find additional applications for the devices and systems disclosed herein aside from use with the medical articles and devices mentioned above. Thus, the illustrations and descriptions of the securement system in connection with the medical articles are merely exemplary of some possible applications of the securement system.

The securement system described herein is especially adapted to arrest lateral and/or transverse movement of a medical article, as well as hold the medical article against the patient. The securement system accomplishes this without meaningfully impairing (i.e., substantially occluding) fluid flow through a medical article such as a catheter. As described below, the securement device to accomplish this includes, among other aspects, a tacky gel or foam retainer configured to deform when pressed against a medical article.

The securement system may further inhibit longitudinal motion of the medical article. For example, the gel retainer may be deformed about the medical article such that a longitudinally facing surface of the medical article abuts the gel retainer, whereby the gel inhibits longitudinal motion of the secured portion of the medical article. In addition, surface friction between the gel retainer and the medical article can inhibit longitudinal motion and/or rotation of the medical article with respect to the securement system.

As will be additionally described below, when the securement device is pressed over a medical article, the gel retainer contacts the medical article and may compress and deform to accommodate an outer surface of the medical article. The outer surface may have a tubular, conical, or any other shape as explained below. By this, a portion of the medical article may be surrounded and closely held by the gel retainer to form a stable mount. Because the medical article may be held on a plurality of sides, movement of the medical article is inhibited.

In some embodiments, the securement system releasably engages the medical article. This allows the medical article to be disconnected from the securement system, and from the patient, for any of a variety of known purposes. For instance, the medical provider may want to remove the medical article from the securement system to ease disconnection of two connected medical articles or to clean the patient.

In some embodiments, at least one securement device of the securement system is not destroyed during disengagement of the securement system. In this way, the securement device can be reused. It is not limited to use for only one medical article, but can be used multiple times for the same medical article or sometimes for different medical articles. The securement system can further be used with multiple medical articles at a single time. For example, two medical lines could be secured by at least some embodiments of the device. The two lines need not be arranged along the same axis to be secured by the device.

The securement system is configured to secure medical articles having a plurality of different shapes and/or sizes. The gel retainer may conform to the shape of a portion of the medical article, thereby allowing medical articles of different sizes and shapes to be securely held on the skin of the patient. For example, the securement system may be used to hold a substantially linear medical article such as a drainage tube against the skin of the patient. The securement system may additionally be used to secure a medical article with an elongated body and a laterally extending surface, such as a winged catheter, or other medical articles that are not substantially linear, for example.

The securement system is further configured to be positioned in a multitude of orientations at a multitude of locations on the patient's body. As described below, the securement device to accomplish this includes, among other aspects, an adhesive configured for attachment to the patient's skin. Depending on the location or desired orientation of the medical article being secured to the patient, the orientation of the securement system can be adjusted and configured by the medical provider.

To assist in the description of components of the securement system, the following terms are used. Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise. Also, the terms "proximal" and "distal," which are used to describe the present securement system, are used consistently with the description of the exemplary applications. Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "bottom" is used to describe a surface of a device that is located nearest the skin of the patient.

The term "alkyl" refers to radicals having from 1 to 8 carbon atoms per alkyl group, such as methyl, ethyl, propyl, butyl, pentyl, hexyl, octyl and the like. The term "alkenyl" refers to radicals having from 2 to 8 carbon atoms such as, vinyl, allyl and 1-propenyl. The term "aryl" refers to mononuclear and binuclear aryl radicals such as, phenyl, tolyl, xylyl, naphthyl and the like; and mononuclear aryl alkyl radicals having from zero (i.e. no alkyl group or a bond) to 8 carbon atoms per alkyl group such as benzyl, phenyl and the like. The term "monovalent hydrocarbon radicals" includes hydrocarbon radicals such as alkyl, alkenyl and aryl.

The term "tacky" refers to an adhesive property that is somewhat sticky to the touch, enabling a gel pad or sheet padding to be readily attached to a limb or other area of a patient's body yet easily removed, i.e. to be releasably attached. The term "macerating" means to soften the skin over a period of time, especially as a result of the skin being wetted or occluded. The term "limb" refers to the paired appendages of the body used especially for movement or grasping, including the legs, knees, shins, ankles, feet, toes, arms, elbows, forearms, wrists, hands, fingers or any part thereof. The term "curing" refers to any process by which raw or uncured polysiloxanes containing reinforcing agents are convened to a finished product, i.e. to form a soft, tacky, reinforced polysiloxane elastomer.

With reference now to FIG. 1A, an embodiment of a securement device 10 includes a body member 20a and a foam or gel retainer. The foam or gel retainer is attached to the body member 20, and in the illustrated embodiment the foam or gel retainer is configured as a gel pad 30 with a thickness that protrudes from the body member 20a. For ease of illustration, the securement device 10 is shown upside down in FIG. 1A. Thus, the gel pad 30 is actually attached to a bottom surface of the body member 20a.

For ease of explanation, like reference numerals are used throughout the figures to indicate like features. Individual letters are added as a suffix to the reference numerals when describing individual or varying embodiments of the features. For example, body members 20a and 20b may comprise like features, as described below, but may be embodied in different configurations, such as characterized by a different shape or size.

Figure 1B:
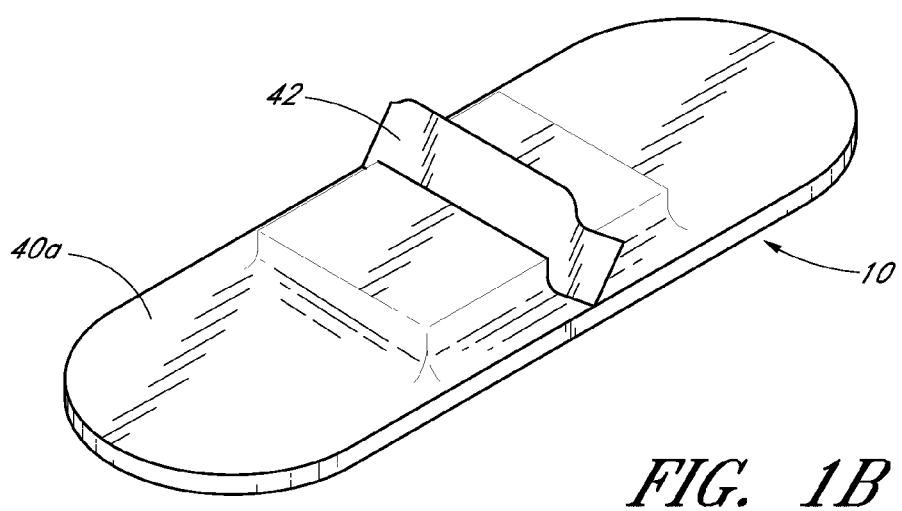
FIG. 1B is a perspective view of the securement device from FIG. 1A with a release liner attached.

As will be described further below, at least a portion of the body member 20a visible in FIG. 1A may comprise an adhesive. In addition, the gel pad 30 may have a tacky property. FIG. 1B shows the securement device 10 with a removeable release liner 40a attached. The release liner 40a covers the adhesive and the gel pad 30 of the securement device 10. The release liner 40a may resist tearing and may be divided into a plurality of pieces to assist removal of the release liner 40a and ease attachment of the securement device 10 to a patient. In the illustrated embodiment, the release liner 40a is sized similarly to the body member 20a. The release liner 40a may, however, be configured as another size or shape. For example, the release liner 40a may be configured such that its edges are exposed beyond the securement device 10 to provide a grasping edge for easy removal of the release liner 40a. In the illustrated embodiment, the release liner 40a is shown as including tab 42 which can be grasped when removing the release liner 40a. The release liner 40a may be made of a paper, plastic, polyester, or similar material. For example, the release liner 40a may comprise a material made of poly-coated, siliconized paper, or another suitable material such as high density polyethylene, polypropylene, polyolefin, or silicon coated paper.

Figure 2:
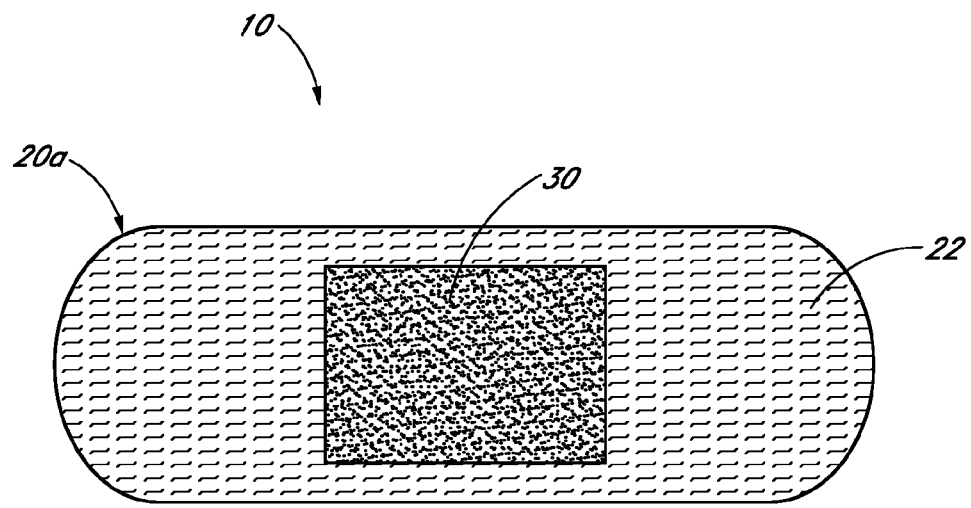
FIG. 2 is a bottom view of the securement device from FIG. 1A.

A bottom surface 22 of the body member 20a, shown in a bottom view of the securement device 10 in FIG. 2, comprises an adhesive. The body member 20a may be configured as an adhesive dressing, or an adhesive may be coated onto the bottom surface 22. In the illustrated embodiment, the adhesive is formed over the extent of the bottom surface 22. In other embodiments, the adhesive may only partially cover the bottom surface 22. For example, the adhesive may be formed as a solid layer or as an intermittent layer such as in a pattern of spots or strips.

The adhesive comprises a compound configured to adhere to the skin of a patient. For example, the adhesive may comprise a medical-grade adhesive that is either diaphoretic or nondiaphoretic, depending upon the particular application. In one embodiment, the adhesive comprises one of the TEGA-DERM line of adhesive dressings, manufactured by 3M. As described above, the adhesive may be covered with a release liner prior to use.

Figure 3:
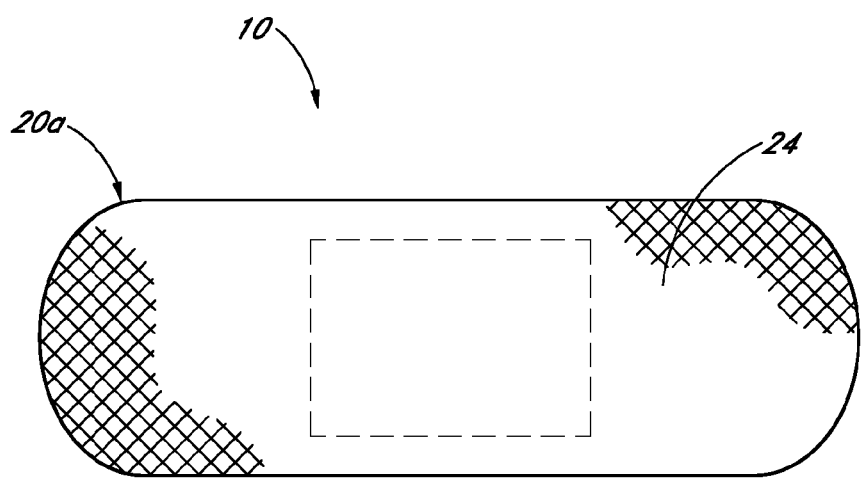
FIG. 3 is a top view of the securement device from FIG. 1A.

A top surface 24 of the body member 20a, located opposite the bottom surface 22 and shown in a top view of the securement device 10 in FIG. 3, may be smooth, textured, or a combination of the two. In one embodiment, the top surface 24 is textured to allow a medical provider to more easily handle and apply the securement device 10.

The body member 20a is configured to be flexible. When placed over a medical device, the body member 20a may be conformed to the shape of the medical device and/or a patient on whom the medical device is placed. The body member 20a may comprise any number of flexible materials. In one embodiment, the body member 20a comprises a foam (e.g., closed-cell polyethylene foam) or woven (e.g., tricot) material.

The body member 20a may be integrally formed, or may be formed as a laminate structure with a bottom layer providing the bottom surface 22 and a top layer providing the top surface 24. In such laminate structure, one or more intermediate layers may be formed between the top layer and bottom layer. For example, a suitable laminate that comprises a foam or woven material with an adhesive layer is available commercially from Avery Dennison of Painsville, Ohio. In one embodiment, the upper surface 24 is provided by an upper paper or other nonwoven cloth layer, and an inner foam layer is placed between the upper layer a lower layer providing the adhesive.

Figure 5:
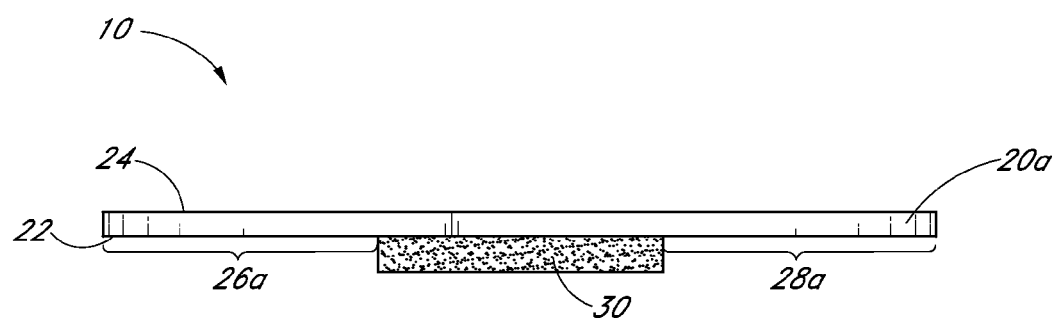
FIG. 5 is a front view of the securement device from FIG. 1A.

The body member 20a may be configured in any number of sizes and shapes. For example, the foam or gel retainer may be attached to a first portion of the bottom surface 22 so that a second portion of the bottom surface 22 is attachable to a patient. As can be seen in a front view of the securement device 10 in FIG. 5, lateral portions 26a and 28a extend beyond the lateral edges of the gel pad 30. When the gel pad 30 is placed over a medical article, one or both of the lateral portions 26a and 28a will contact and adhere to the skin of a patient such that the securement device 10 and the medical article is attached to the patient. The lateral portions 26a and 28a may be sized to provide a sufficient surface area to attach to the patient such that the securement device 10 will not detach when the secured medical article is manipulated or adjusted during normal movement of the patient. In the illustrated embodiment, the ends of the lateral portions 26a and 28a are rounded. In other embodiments, the end of one or both of the lateral portions 26a and 28a is squared, pointed, or is configured as another shape.

The foam or gel retainer of the securement system 10 has a suitably high coefficient of friction and hardness for securing a medical device. The foam or gel retainer is configured to deform when pressed against a medical article and may encase a portion of the medical article. The foam or gel retainer may be a soft die-cut material.

The size and shape of the foam or gel retainer is not limited to the illustrated embodiments. For example, the foam or gel retainer may be formed into a pad, as with the gel pad 30, or may be shaped as a post configured to secure a medical device, for example a catheter. The foam or gel retainer may be rectangular, oval, circular, trapezoidal, or square, although other shapes can be employed depending upon the particular application.

In one embodiment, the foam or gel retainer comprises a viscoelastic memory foam. The memory foam may be made from polyurethane with additional chemical additives that add to its viscosity level, thereby increasing the density of the foam. Depending on the chemicals used and the overall density of the foam, it can be firmer in cooler temperatures and softer in warmer environments. As will be appreciated, higher density memory foam will react with body heat to allow it to mold itself to the shape of a warm body. The memory foam may be configured to distribute pressure when placed over a medical article, and in some embodiments is configured to retain heat, thereby increasing pain relief in some patients. Those skilled in the art will understand how to construct the memory foam from the foregoing description.

The foam or gel retainer may comprise a cured, tacky, reinforced polysiloxane elastomer. In such embodiment, the gel pad 30 may be formed by curing a mixture of a lower alkenyl-functional polysiloxane, such as a vinyl containing polysiloxane, and a hydrogen containing polysiloxane copolymer containing active hydrogen groups. In this regard, the term "hydrogen" refers to active hydrogen that is directly bonded to a silicon atom (Si—H), for example, silicon hydrides and hydrogen containing organopolysiloxanes. Such amounts of the hydrogen containing polysiloxane copolymer will be dependent upon factors such as the molar ratio of alkenyl radicals to active hydrogen in the uncured composition and the nature of these components, including such variables as polymer chain length, molecular weight and polymer structure.

The organopolysiloxane elastomers disclosed herein, prior to curing, have a ratio of hydrogen to alkenyl radicals of less than 1.5, or 0.5 to 1.2, which imparts tack or tackiness to the end product produced therefrom. The tackiness is believed to be caused by the partially crosslinked organopolysiloxane elastomers.

It should be recognized that the tacky gel pad 30 possesses the requisite tacky property throughout the entire gel pad 30. However, surface tack can be modified to be greater than or less than the interior tack. Quantitative measurements of tackiness can be made using a suitable tack tester, such as a Polyken® probe tack tester, a rolling ball tack tester, a peel tester or combinations thereof. Tack can be tested with the Polyken® probe tester in accordance with any suitable procedure, such as American Society For Testing and Materials (ASTM) Designation: D2979-71 (Reapproved 1982), Standard Test Method for Pressure-Sensitive Tack of Adhesives Using an Inverted Probe Machine, pp. 187-189, from the Annual Book of ASTM Standards, Vol. 15.09. The Polyken® probe tack tester is the trademark of the Kendall Company, under license by Testing Machines Inc., Mineola, Long Island, N.Y. Tack can also be tested with a rolling ball tack tester in accordance with Pressure Sensitive Tape Council, Test Methods for Pressure Sensitive Tapes, 9th Edition, PSTC-6, revised August, 1989, pp. 29-30 or ASTM D3121. Tack can also be tested with a peel tester in accordance with Pressure Sensitive Tape Council, Test Methods for Pressure Sensitive Tapes, 9th Edition, PSTC-1, revised August 1989, pp. 21-22. The tacky, cushioning layer can be artificially aged prior to tack testing using conventional accelerating aging procedures, such as by exposing the layer to ultraviolet light, elevated temperatures and/or elevated humidity.

The tacky gel pad 30 disclosed herein has little or no ability to induce maceration of the skin, due in part, to its permeability for transporting water vapor from the skin through the gel pad. Thus, the tacky layer disclosed herein can provide a third, tri-function of inducing little or no maceration when applied to the skin for an extended period. One test method for evaluating water vapor transmission is ASTM Designation: E96-80, Standard Test Methods for Water Vapor Transmission of Materials, edited May 1987, pp. 629-633.

Determinations of the hardness of the gel pad 30 can be made with any suitable durometer for testing hardness. One test method entails resting the edge of a Shore 00 durometer on a material, applying a presser foot to the material without shock and taking the average of three readings. Further details for testing hardness can be found in ASTM Test Method D2240. One of ordinary skill in the art will appreciate that elastomers measured by the Shore 00 durometer scale are softer than those measured by the Shore A durometer scale.

Representative vinyl-containing high viscosity organopolysiloxanes of formula (1) suitable for preparing a base material include, but are not limited to the following.

$$R^4-S^4-\underset{\underset{R}{|}}{\overset{\overset{R^1}{|}}{O}Si}-\underset{\underset{R_x}{|}}{\overset{\overset{R}{|}}{O}Si}-\underset{\underset{R_y}{|}}{\overset{\overset{R^2}{|}}{O}Si}-\underset{\underset{R}{|}}{\overset{\overset{R^1}{|}}{O}Si}-R^5 \quad (1)$$

| Polymer | R | $R^2$ | $R^3$ | $R^4$ | $R^5$ | x | y |
|---|---|---|---|---|---|---|---|
| 1 | —$CH_3$ | —$CH_3$ | —$C_6H_5$ | —$CH_3$ | —$C_2H_3$ | 925 | 50 |
| 2 | —$CH_3$ | —$CH_3$ | —$C_6H_5$ | —$C_2H_3$ | —$C_2H_3$ | 809 | 45 |
| 3 | —$CH_3$ | —$CH_3$ | —$C_6H_5$ | —$C_2H_3$ | —$C_2H_3$ | 611 | 41 |
| 4 | —$CH_3$ | —$CH_3$ | —$C_6H_5$ | —$C_2H_3$ | —$C_2H_5$ | 471 | 30 |
| 5 | —$CH_3$ | —$CH_3$ | —$CH_3$ | —$C_2H_3$ | —$CH_3$ | 600 | 20 |
| 6 | —$CH_3$ | —$CH_3$ | —$CH_3$ | —$C_2H_3$ | —$C_2H_5$ | 600 | 20 |

Representative low viscosity organopolysiloxanes of formula (2) suitable for use in preparing a base material include, but are not limited to the following.

$$R^1-Si-\underset{\underset{R}{|}}{\overset{\overset{R^3}{|}}{O}Si}-\underset{\underset{R_w}{|}}{\overset{\overset{R}{|}}{O}Si}-\underset{\underset{R_z}{|}}{\overset{\overset{R^2}{|}}{O}Si}-\underset{\underset{R}{|}}{\overset{\overset{R^3}{|}}{O}Si}-R^6 \quad (2)$$

| Polymer | R | $R^2$ | $R^3$ | $R^4$ | $R^6$ | x | z |
|---|---|---|---|---|---|---|---|
| 1 | —$CH_3$ | —$C_2H_3$ | —$C_6H_5$ | —$CH_3$ | —$CH_3$ | 138 | 13 |
| 2 | —$CH_3$ | —$C_2H_3$ | —$C_6H_5$ | —$CH_3$ | —$CH_3$ | 192 | 39 |
| 3 | —$CH_3$ | —$C_2H_3$ | —$CH_3$ | —$CH_3$ | —$CH_3$ | 125 | 25 |
| 4 | —$CH_3$ | —$CH_3$ | —$CH_3$ | —$CH_3$ | —$CH_3$ | 90 | 20 |
| 5 | —$CH_3$ | —$CH_3$ | —$CH_3$ | —$CH_3$ | —$CH_3$ | 125 | 25 |

The base material prepared from the vinyl-containing high viscosity organopolysiloxanes of formula (1) and the low viscosity organopolysiloxanes of formula (2) can be admixed with a copolymer containing dimethyl and methyl hydrogen siloxanes. The amount of hydrogen-containing organopolysiloxane used should be sufficient to achieve a ratio of alkenyl radicals to hydrogen in the uncured composition of less than 1.2.

The elastomers are reinforced with a suitable reinforcing agent or filler such as titanium dioxide, calcium carbonate, lithopone, zinc oxide, zirconium silicate, silica aerogel, iron oxide, diatomaceous earth, silazane-treated silica, precipitated silica, fumed silica, mined silica, glass fibers, magnesium oxide, chromic oxide, zirconium oxide, aluminum oxide, alpha quartz, calcined clay and the like, as well as various reinforcing silica fillers taught in U.S. Pat. No. 3,635,743, the contents of which are hereby incorporated by reference in their entirety, or mixtures of any of the above, or a filler selected from silazane treated silica, precipitated silica and fumed silica or mixtures thereof. In one form, the reinforcing filler is a highly reinforcing silica filler with a surface area ranging from about 80 to about 400 square meters/gram ($m^2/g$), or from about 200 to about 400 $m^2/g$. Typically the reinforcing agent is mixed with the vinyl-containing high viscosity organopolysiloxane (1) and low viscosity organopolysiloxane (2) prior to addition of the hydrogen containing polysiloxane copolymer. The reinforcing filler can be employed in the uncured composition in an amount ranging from 10 parts to about 70 parts per 100 parts of the uncured composition, or from 15 parts to about 40 parts, or from about 20 to about 30 parts. In the cured tacky, reinforced cushioning layer, such amounts correspond to about 10% to about 70% by weight, or from about 15% to about 40%, or from about 20% to about 30%.

The durometer or hardness of the polysiloxane elastomers disclosed herein can be lowered (i.e. made softer) by incorporating low viscosity polysiloxanes into the uncured composition. Representative low viscosity polysiloxanes include polydimethylsiloxane fluids or vinyl-containing polydimethylsiloxane fluids. The molecular weight average of the plasticizer can range from about 750 to about 30,000. The low viscosity polysiloxanes can be employed in an amount ranging from about zero to about 50% by weight of the uncured composition, or from about 10% to about 30%.

The polysiloxane elastomers disclosed herein possess suitable hardness, tensile strength, elongation and tear strength, as based upon standard elastic materials testing. Unreinforced polysiloxane compositions are enclosed in an envelope or other supporting means, i.e. foam impregnation, in order to maintain the shape or durability of an article produced therefrom. In contrast, the high coefficient of friction, tacky, polysiloxane gel pad 30 disclosed herein is viscoelastic and has a measurable hardness, tensile strength, elongation and/or tear strength.

Further, the tacky, reinforced polysiloxanes disclosed herein can retain their elastic properties after prolonged action of compressive stresses, a property known as compression set. Compression set is an indicator of durability. According to ASTM Designation: D395-85, Standard Test Methods for Rubber Property Compression Set, pp. 34-35, the actual stressing service may involve the maintenance of a definite deflection, the constant application of a known force, or the rapidly repeated deformation and recovery resulting from intermittent compressive forces. Though the latter dynamic stressing, like the others, produces compression set, its effects as a whole are simulated more closely by compression flexing or hysteresis tests. Therefore, compression set tests are considered to be mainly applicable to service conditions involving static stresses.

Tests are frequently conducted at elevated temperatures. In a first method utilizing static stresses, a test specimen is compressed to a deflection and maintained under this condition for a specified time and at a specified temperature. In a second method utilizing static stresses, a specified force is maintained under this condition for a specified time and at a specified temperature. After application of the specified deflection or specified force the residual deformation of a test specimen is measured 30 minutes after removal from a suitable compression device in which the specimen has been subjected for a definite time to compressive deformation under specified conditions. After measurement of the residual deformation, the compression set as specified in the appropriate method is calculated according to ASTM D395-85 equations.

When produced in accordance herewith, the gel pad 30 may be prepared to exhibit the following physical properties: a durometer hardness of from about 5 units to about 55 units (Shore 00), a tensile strength of from about 20 psi to about 800 psi, a minimum elongation of from about 250% to about 1100%, a tear strength of from about 5 lb/in to about 200 lb/in, a polyken probe tack of about 10 grams to about 450 grams, a rolling ball tack of about 0 to about 3 inches and a peel test value of from about 0.02 lb/in to about 80 lb/in. The gel pad 30, however, is of course not limited to the above described properties.

The gel pad 30 can be prepared using techniques such as molding, liquid injection molding, transfer molding, casting and the like. The gel pad 30 can be preformed into a desired shape for use with the securement system 10 or gel material may be supplied in a sheet form which may be cut to the desired shape prior to use and attached to the body member 20a. A gel material may also be provided in a kit form, where a catalyst may be provided in a first container and other components are premixed and provided in a second container. In the kit, a mold is provided and the components may be mixed, poured into the mold, and cured. Curing can be with or without heat.

Such curing can be achieved by increasing the molecular weight of the uncured polysiloxane elastomers to the extent desired through crosslinking, using heating or standing at ambient temperatures, as described U.S. Pat. No. 3,445,420, the contents of which are hereby incorporated by reference in their entirety. Generally, the degree to which the uncured polysiloxane composition can be partially crosslinked can range from about 30% to about 90%, based upon the alkenyl-containing polysiloxane, or from about 30 to about 60%.

In the illustrated embodiment, the gel pad 30 is centered on the body member 20a, as can be seen in the top view of the securement device 10 in FIG. 2. In this embodiment, the lateral portions 26a and 28a of the bottom surface 22 may be used to secure the securement device 10 to a patient. Of course, the gel pad 30 may be positioned in another location besides being centrally located. In one embodiment in which the gel pad 30 is configured to self adhere to the patient, the gel pad 30 may be coextensive with the entire bottom surface 22 of the body member 20a.

Figure 4:
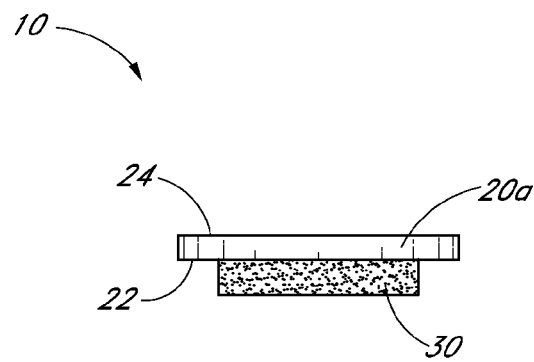
FIG. 4 is a side view of the securement device from FIG. 1A.

As can be seen in a side view of the securement device 10 in FIG. 4, the gel pad 30 protrudes from the body member 20a. When a medical article is pressed against the gel pad 30, the gel pad will deform at least towards to the body member 20a and may partially surround or encase at least a portion of the medical article. As can be seen in the side view of the medical device 10 in FIG. 4 and the front view of the medical device 10 in FIG. 5, the gel pad 30 is configured to have a uniform thickness. In other embodiments, the thickness of the gel pad 30 may fluctuate across the length and/or width of the gel pad 30.

Figure 6:
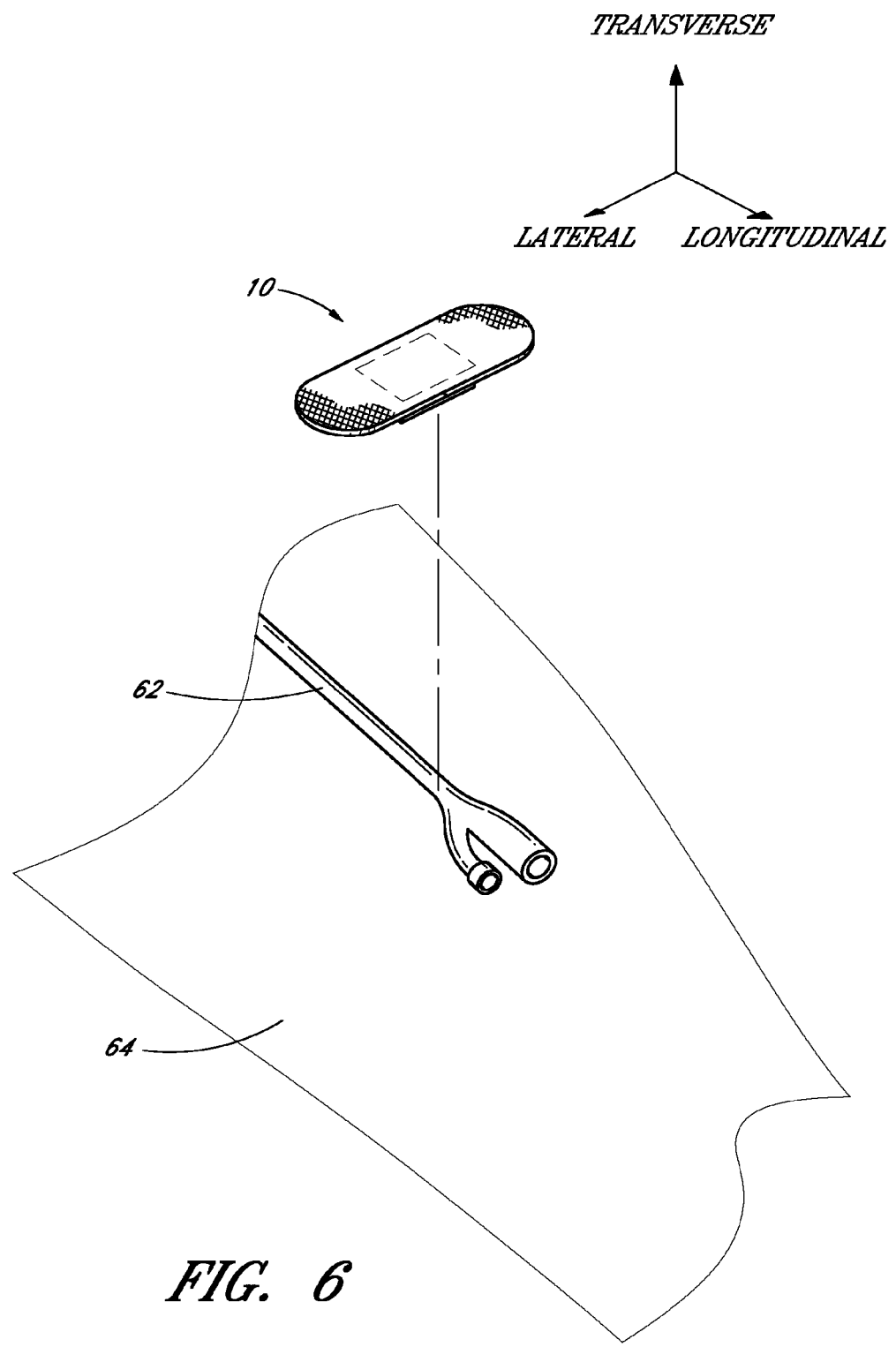
FIG. 6 is a perspective view of the securement device from FIG. 1A positioned above a medical article placed on a patient's skin.
Figure 7:
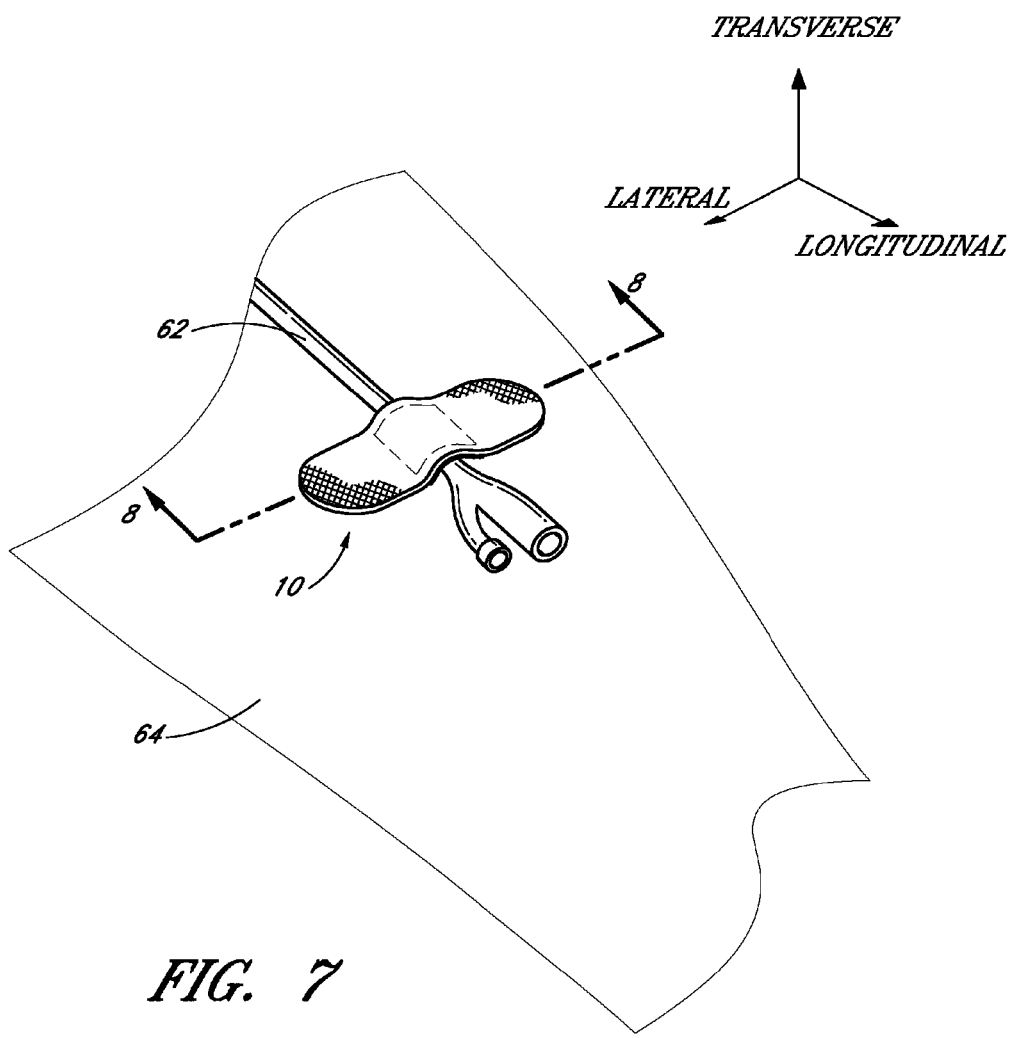
FIG. 7 is a perspective view of the securement device from FIG. 1A secured over the medical article.

A medical article can be secured to a patient by the securement device 10, as shown in FIGS. 6 and 7. In the illustrated embodiment, the medical article is a Foley catheter 62 placed on the skin of a patient's leg 64. In the figures, a "longitudinal axis" is generally parallel to a lumen of the medical article. A "transverse axis" is normal to the longitudinal axis and extends in a direction generally parallel to the line shown extending between the securement device 10 and the catheter 62 in FIG. 6. A "lateral axis" extends normal to both the longitudinal and transverse axes. The "longitudinal direction" refers to a direction substantially parallel to the longitudinal axis; "the transverse direction" refers to a direction substantially parallel to the transverse axis; and "the lateral direction" refers to a direction substantially parallel to the transverse axis.

After placing the securement device 10 above the catheter 62, as shown in FIG. 6, a medical provider can then lower the securement device 10 over the medial article 62. The medical provider presses the securement device 10 against the patient such that the gel pad 30 presses against the catheter 62 and such that the adhesive on the bottom surface 22 adheres to the skin of the patient's leg 64. The catheter 62 will thus be held on the patient by the securement device 10, as shown in FIG. 7.

Figure 8:
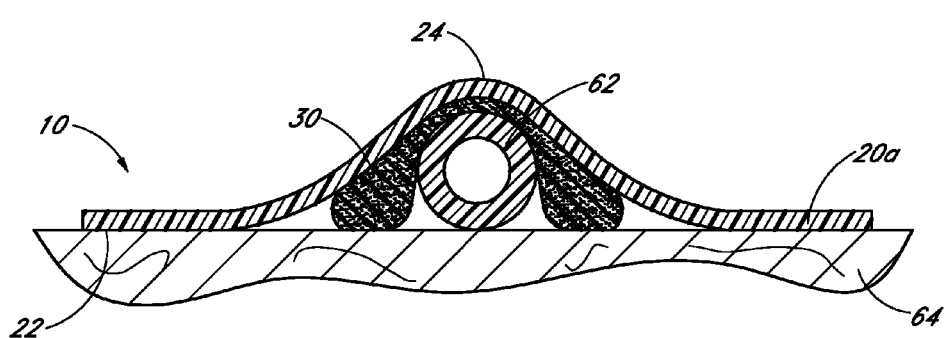
FIG. 8 is a cross-section view taken along line 8-8 of FIG. 7 and shows the gel pad deformed about the medical article.

As can be seen in a cross-section view taken along line 8-8 of FIG. 7, which cross-section view is illustrated in FIG. 8, the gel pad 30 conforms to the shape of an outer surface of the catheter 62. In this way, the gel pad 30 may at least partially encase the catheter 62 without substantially occluding the catheter 62. As described above in relation to the gel pad 30, the gel pad 30 may return to its original shape when removed from contact with the catheter 62. In other embodiments, the gel pad 30 may substantially retain the shape into which it has conformed. In yet other embodiments, the gel or foam retainer may be formed to have a predefined contour therein to accept a medical article of a certain shape.

Attaching the catheter 62 to the patient in this way inhibits at least lateral movement of the catheter 62. The catheter 62 is at least partially surrounded by the gel pad 30 and abuts the gel pad 30. The gel pad 30 may be in contact with the patient's skin, which may further inhibit motion of the securement device 10, for example due to a tackiness of the gel pad 30. In addition, transverse motion of the catheter 62 is inhibited by the securement device 10 being adhered to the patient.

The securement device 10 may also inhibit longitudinal motion of the catheter 62 when pressed against the medical article. As described above, the gel pad 30 has a tacky property with a high coefficient of friction that inhibits the catheter 62 from sliding longitudinally beneath the securement device 10. In addition, this tacky property will inhibit rotation of the catheter 62. In some embodiments, the portions of the gel pad 30 contacting the patient's skin self adhere to the patient's skin, further securing the medical article on the patient. In the embodiments in which the gel pad 30 is configured to at least partially adhere to the catheter 62, the medical provider may first press the catheter 62 against the gel pad 30 to secure the catheter 62, and then place the combination of the catheter 62 and the securement device 10 onto the skin of the patient, instead of first placing the catheter 62 on the skin of the patient.

Figure 9:
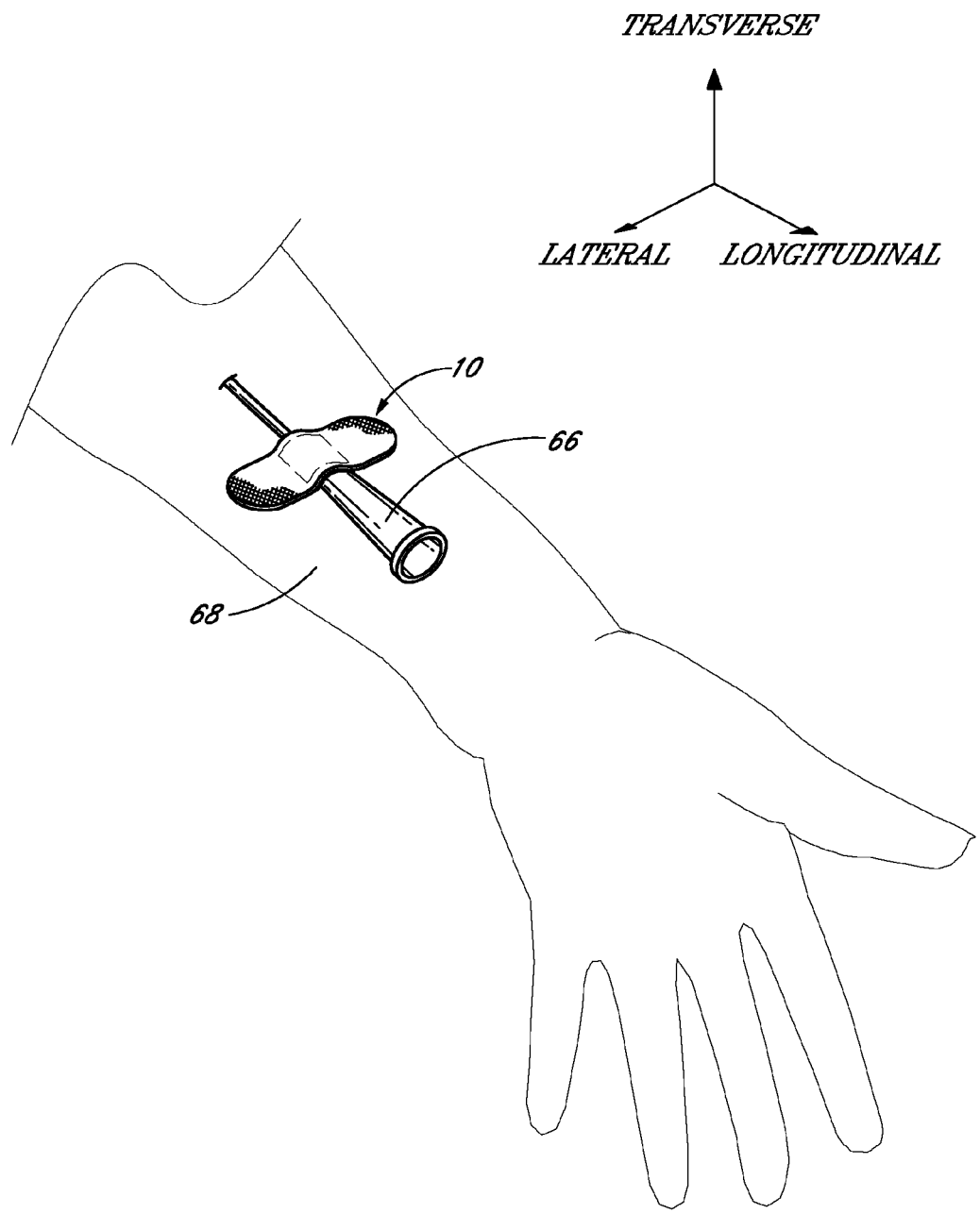
FIG. 9 is a perspective view of the securement device from FIG. 1A secured over another medical article.

The securement device 10 can attach a variety of medical articles, singularly or in combination, in position upon a patient. For example, as can be seen in FIG. 9, the securement device 10 can be used to hold a medical article different from that of the Foley catheter 62. In the illustrated embodiment, the securement device 10 is shown as securing a catheter hub 66 to the skin of a patient's arm 68. Due to the flexibility of the body member 20a and the viscoelasticity of the gel pad 30, the securement device can secure any other number of medical devices as well at any number of different positions on the patient. As will be appreciated by one of skill in the art, the configuration of the securement device 10 allows the securement device 10 to not only secure this variety of medical articles, but also to secure them in a variety of different orientations.

In some embodiments, the securement device 10 can be used to hold several medical articles. For example, the gel pad 30 may have a size sufficient to encase several medical articles. In this situation, operation of the securement device 10 is not changed. The securement device 10 can be pressed down over the medical articles to engage the medical articles and adhere to the skin of the patient. The medical articles may or may not be parallel in configuration.

In some embodiments, the securement device 10 is configured to semi-permanently attach to the patient. In other embodiments, the securement device 10 is configured to be removable such that the medical article may be adjusted or replaced, such as with a similar medical article, with a medical article of a different size or shape, or with several medical articles. In this embodiment, the medical provider may peel the securement device 10 from the skin of the patient to remove or reposition the medical article. In some embodiments, the gel pad 30 is configured to be separable from the medical article without leaving a residue, for example, without leaving a sticky deposit on the medical article.

Figure 10A:
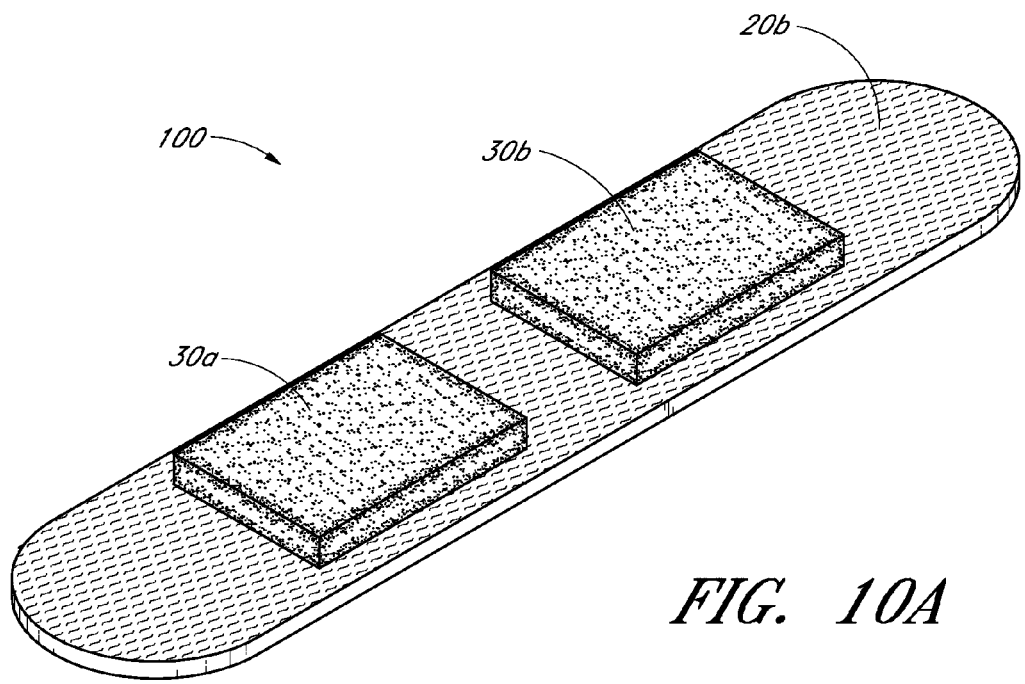
FIG. 10A is a perspective view of a securement device in accordance with another embodiment of the present invention and shows a plurality of gel pads.

With reference now to FIG. 10A, an embodiment of a securement device 100 includes a body member 20b and a plurality of gel pads 30a and 30b. The gel pads 30a and 30b are attached to the body member 20b, and in the illustrated embodiment the gel pads 30a and 30b are configured with a thickness that protrudes from the body member 20b. For ease of illustration, the securement device 100 is shown upside down in FIG. 10A. Thus, the gel pads 30a and 30b are actually attached to a bottom surface of the body member 20b.

Figure 10B:
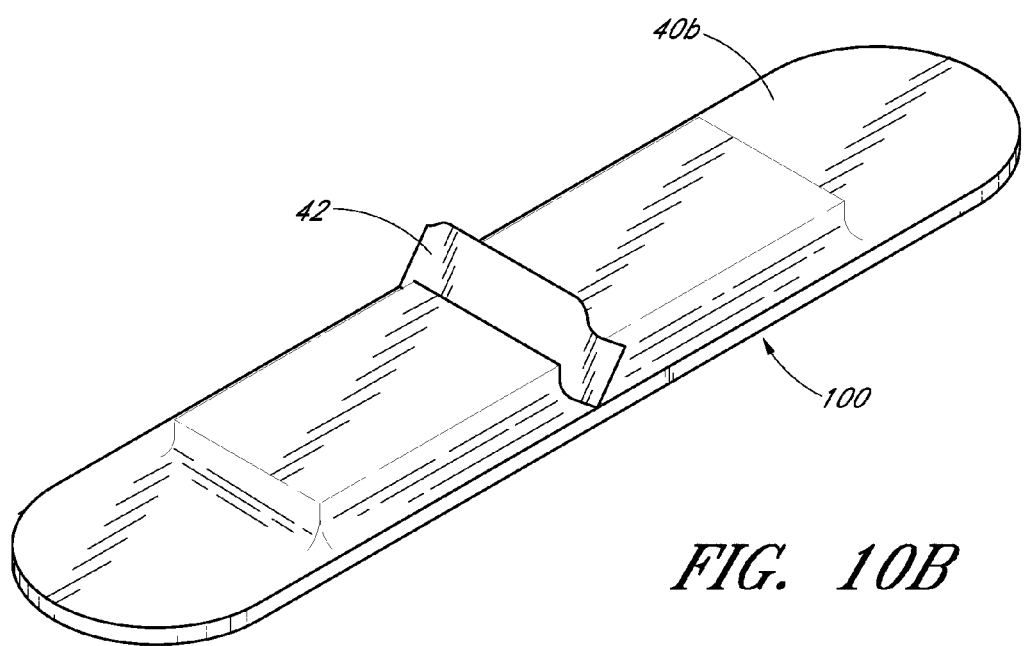
FIG. 10B is a perspective view of the securement device from FIG. 10A with a release liner attached.

FIG. 10B shows the securement device 100 with a removeable release liner 40b attached. The release liner 40b covers the gel pads 30a and 30b and adhesive portions of the body member 20b. In other embodiments, several release liners may be attached to the securement device 100. For example, there may be separate release liners to cover each of the gel pads 30a and 30b or to cover separate adhesive portions on the body member 20b. In the illustrated embodiment, the release liner is configured to have a shape that roughly corresponds to the shape of the body member 20b, and is longer than the release liner 40a illustrated in FIG. 1B. The release liner 40b may otherwise be configured similar to the release liner 40a.

In the illustrated embodiment, the securement device includes two gel pads 30a and 30b, which are configured similar to the gel pad 30 described above. In other embodiments, the securement device 100 may include other embodiments of a foam or gel retainer, or both a gel pad and other foam or gel retainer. In some embodiments, the securement device 100 includes more than two gel pads or other foam or gel retainers. The gel pads or other foam or gel retainers may be arranged in any number of configurations on the body member 20b. The gel pads or other foam or gel retainers may be configured to secure one or more medical articles.

Figure 11:
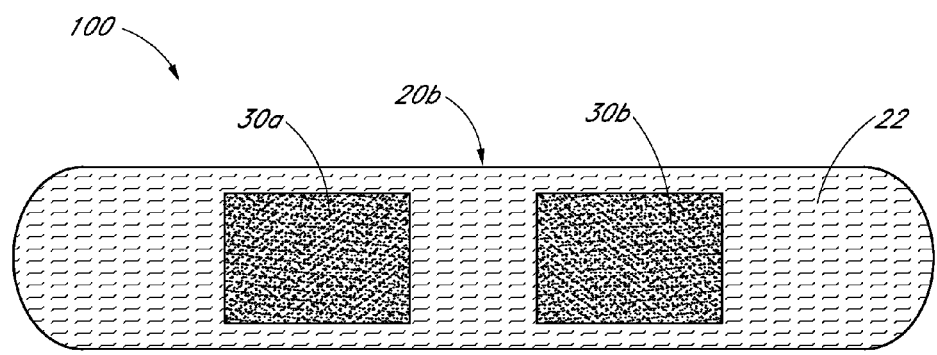
FIG. 11 is a bottom view of the securement device from FIG. 10A.
Figure 14:
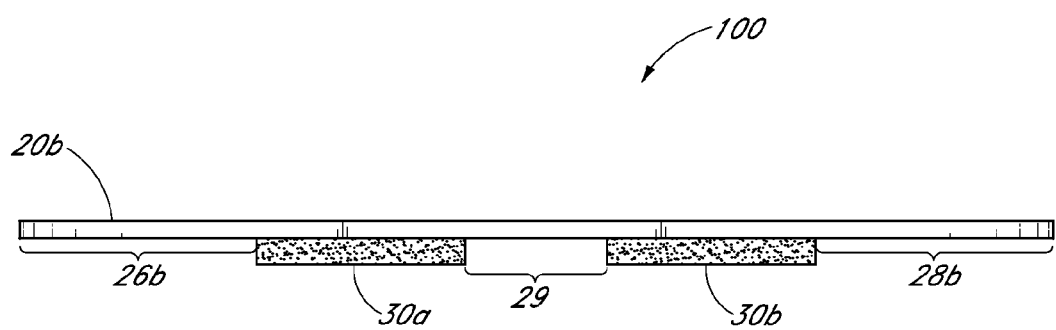
FIG. 14 is a front view of the securement device from FIG. 10A.

As shown in a top view of the securement device 100 in FIG. 11, the body member 20b is configured in a size and shape such that the two gel pads 30a and 30b may be attached to the bottom surface 22 of the body member 20b. As can be seen in front view of the securement device 100 in FIG. 14, lateral portions 26b and 28b of the illustrated embodiment extend beyond the gel pads 30a and 30b, respectively, and intermediate portion 29 extends between the gel pads 30a and 30b. As will be described in more detail below, the intermediate portion 29 may be configured to contact a portion of a medical article.

The intermediate portion 29 may be configured in any number of lengths. In one embodiment, the intermediate portion 29 is configured to accept a portion of a body of a medical article, for example the body of a winged catheter. In other embodiments, the intermediate portion 29 is configured such that two medicals articles, each secured by one of the gel pads 30a and 30b, will be spaced apart at desired or a predetermined distance. Any foam or gel retainers attached to the body member 20b in addition to the gel pads 30a and 30b may be separated from each other and/or the gel pads 30a and 30b by similarly or differently configured intermediate portions.

The bottom surface 22 of the body member 20b comprises an adhesive at one or more of the lateral portions 26 and 28b and the intermediate portion 29. In the illustrated embodiment, the bottom surface 22 comprises an adhesive that is coextensive with the body member 20b. Thus, as illustrated, the bottom surface 22 at all of the lateral portions 26b and 28b and the intermediate portion 29 comprise an adhesive. In some embodiments, the bottom surface 22 at the intermediate portion 29 comprises an adhesive configured to adhere to a patient's skin. In some embodiments, the bottom surface 22 at the intermediate portion 29 comprises an adhesive configured to adhere to a medical article, or does not comprise any adhesive. In some embodiments, the bottom surface 22 at one or more of the lateral portions 26b and 28b does not comprise an adhesive.

Figure 12:
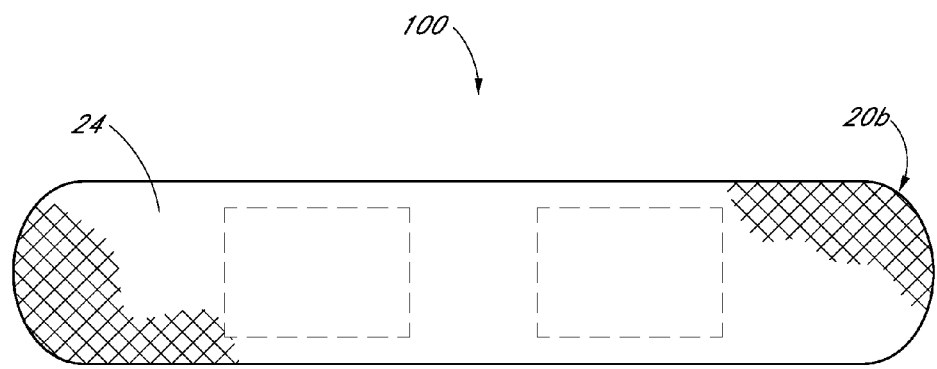
FIG. 12 is a top view of the securement device from FIG. 10A.
Figure 13:
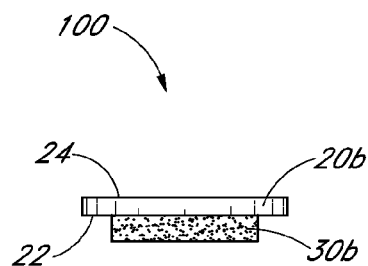
FIG. 13 is a side view of the securement device from FIG. 10A.

As can be seen in a top view of the securement device 100 in FIG. 12 and a side view of the securement device 100 in FIG. 13, the body member 20b may otherwise be configured similar to the body member 20a described above. For example, the ends of the lateral portions 26b and 28b may be shaped in various configurations or the body member 20b may comprise a foam or woven material.

Figure 15:
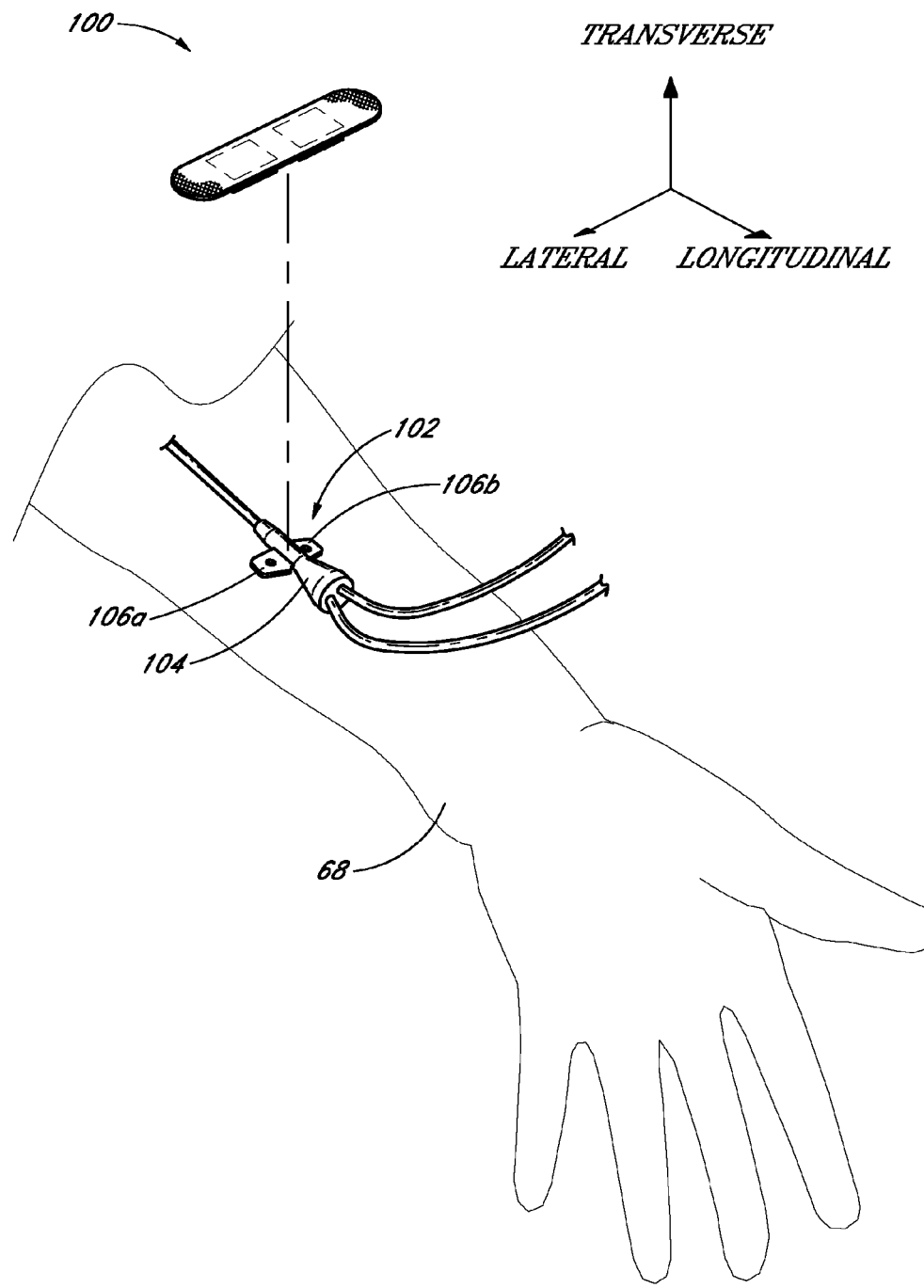
FIG. 15 is a perspective view of the securement device from FIG. 10A positioned above a medical article placed on a patient's skin.
Figure 16:
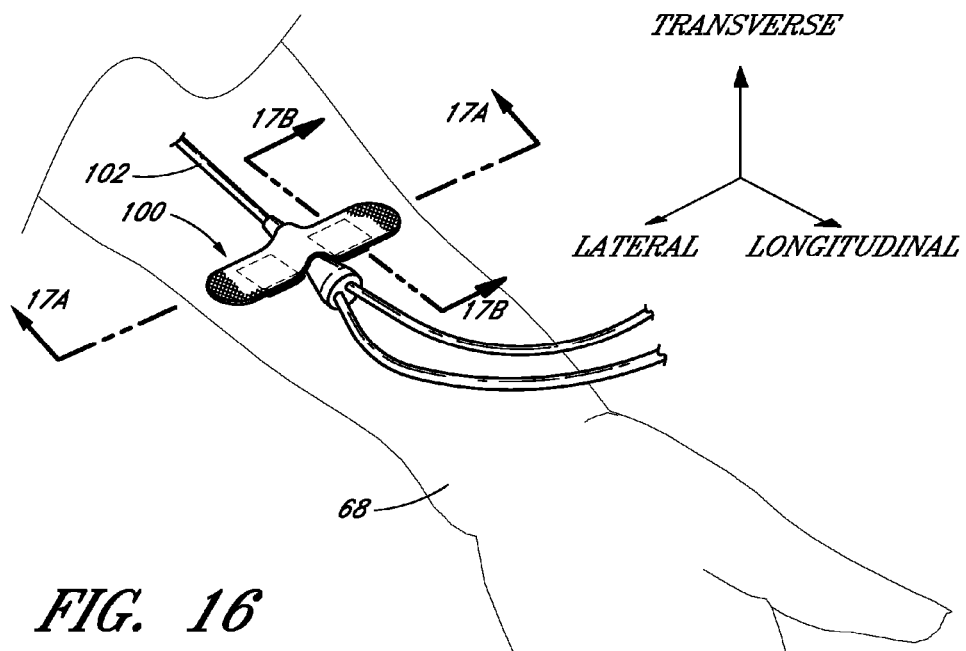
FIG. 16 is a perspective view of the securement device from FIG. 10A secured over the medical article.

A medical article can be secured to a patient by the securement device 100, as shown in FIGS. 15 and 16. In the illustrated embodiment, the medical article is shown as a peripherally inserted central catheter (PICC) 102 placed on the skin of the patient's arm 68. The PICC 102 is illustrated as having dual lumens, a body portion 104, and wings 106a and 106b projecting laterally from the body portion 104.

The method of attaching a medical article to a patient using the securement device 100 is similar to the method of attaching a medical article to a patient using the securement device 10. When contacting the medical article with the securement device 100, however, the gel pads 30a and 30b may be arranged in a number of different configurations with respect to the medical article. In the embodiment illustrated in FIG. 16, the securement device 100 is placed laterally over the PICC 102 to cover the wings 106a and 106b and a segment of the body portion 104.

Figure 17A:
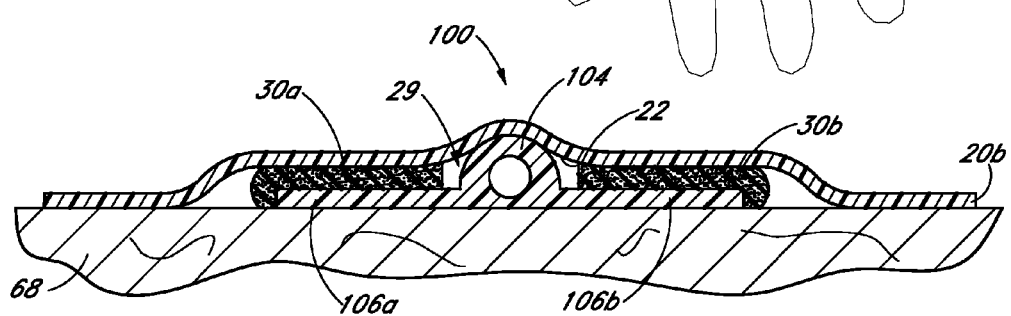
FIG. 17A is a cross-section view taken along line 17A-17A of FIG. 16 and shows the plurality of gel pads laterally deformed about the medical article.

As can be seen in a cross-section view taken along line 17A-17A of FIG. 16, which cross-section view is illustrated in FIG. 17A, gel pads 30a and 30b may conform to the shape of the wings 106a and 106b. The gel pads 30a and 30b are shown as being compressed in the transverse direction and as surrounding lateral facing surfaces of the wings 106a and 106b, which may inhibit at least lateral movement of the PICC 102. In the illustrated embodiment, the body portion 104 is located between the gel pads 30a and 30b so as to contact the bottom surface 22 of the body member 20b at the intermediate portion 29. The bottom surface 22 at the intermediate portion may comprise an adhesive configured to attach to a medical article. Adhering the securement device 100 to the PICC 102 may aid in securement of the PICC 102 and inhibit lateral and/or longitudinal motion of the PICC 102. In other embodiments, the adhesive of the bottom surface 22 at the intermediate portion 29 may be omitted, or the bottom surface 22 at the intermediate portion 29 may be otherwise configured to avoid adhering to the PICC 102.

Figure 17B:
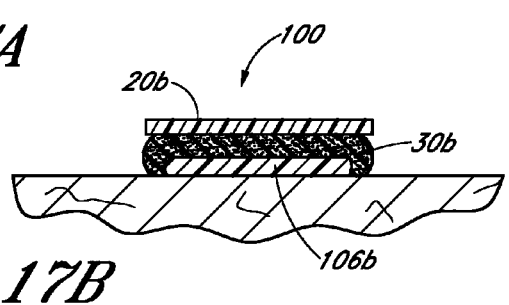
FIG. 17B is a cross-section view taken along line 17B-17B of FIG. 16 and shows one of the plurality of gel pads longitudinally deformed about the medical article.

As can be seen in a cross-section view taken along line 17B-17B of FIG. 16, which cross-section view is illustrated in FIG. 17B, gel pad 30b may surround longitudinally facing surfaces of the wing 106b. Longitudinally facing surfaces of the wing 106a may similarly be surrounded by the gel pad 30a. Such configuration may further inhibit at least longitudinal motion of the PICC 102, for example by placing such longitudinally facing surfaces of the wings 106a and/or 106b in abutment with the gel pad 30a and/or 30b. In other embodiments, the gel pads 30a and 30b may only surround one longitudinally facing surface of one or more of the wings 106a and 106b or no longitudinally facing surface.

In FIG. 17B, the body member 20b is illustrated as having a size such that the body member is not in contact with the patient's skin on either side of the longitudinally facing surfaces of the wing 106b. The body member 20b, however, may be of a size or shape such that the body member 20b will extend sufficient beyond the gel pad 30b to contact the skin of the patient's skin on one or more of these sides. The body member 20b may be similarly configured with respect to the gel pad 30a.

In other embodiments, the PICC 102 may be arranged such that one or more of the wings 106a and 106b contact the body portion 104. Additionally, the securement device 100 could be placed longitudinally over the PICC 102. In such placement, the gel pads 30a and 30b may each contact a portion of a lumen of the PICC 102, while the intermediate portion 29 may contact the body portion 104. In yet other embodiments, a single gel pad attached to the body member 20b could contact the securement device 100, and the single gel pad may have a size sufficient to both laterally and longitudinally surround the securement device 100. These embodiments are merely example configurations of course, and as described above the securement device 100 may be configured with any number of foam or gel retainers and may be placed in a multitude of different configurations to secure many types of medical articles. Use of the securement device 100 to secure such medical articles will not occlude the medical articles, and more than one medical article may be secured at a time.

Figure 18A:
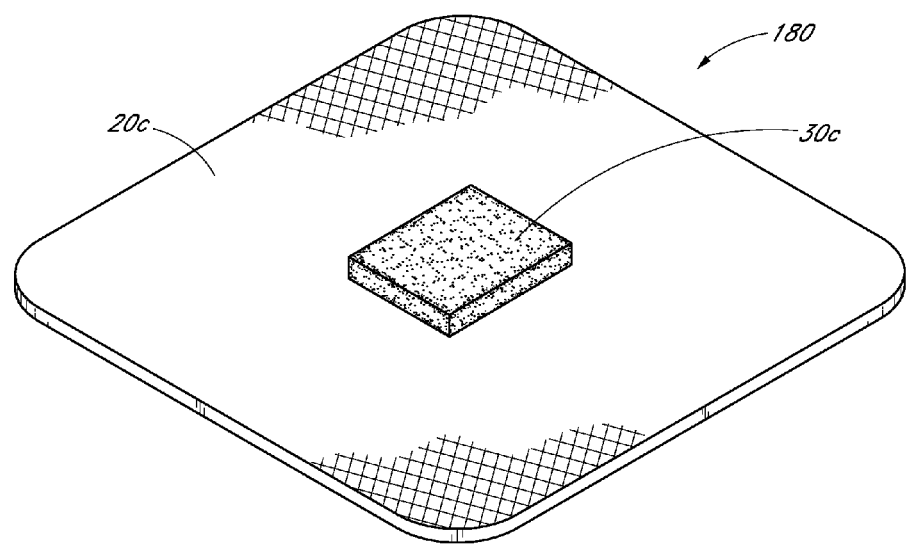
FIG. 18A is a perspective view of a securement device in accordance with another embodiment of the present invention and shows a gel pad.

With reference now to FIG. 18A, an embodiment of a securement device 180 includes a body member 20c and a gel pad 30c. The gel pad 30c is attached to the body member 20c, and in the illustrated embodiment the gel pad 30c is configured with a thickness that protrudes from the body member 20c. The gel pad 30c is configured similar to the gel pad 30, illustrated in FIG. 1A.

Figure 18B:
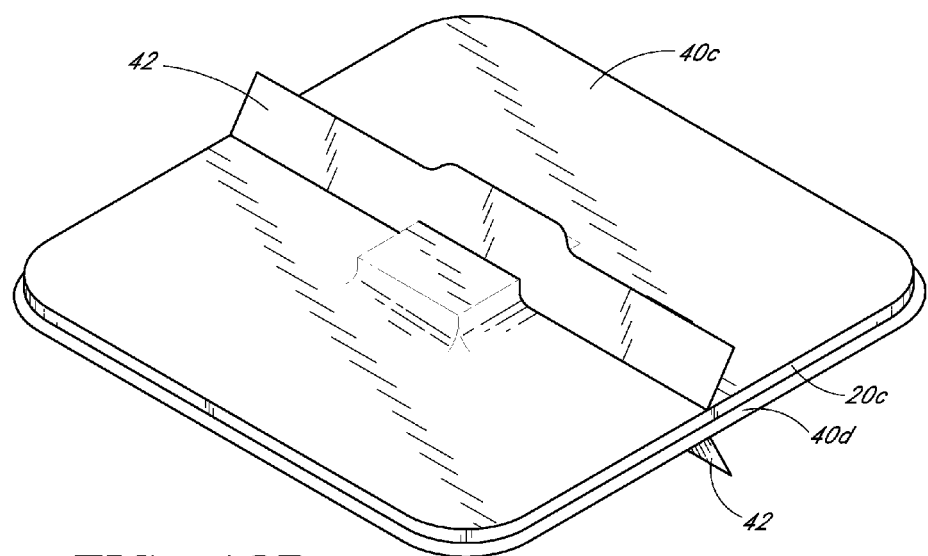
FIG. 18B is a perspective view of the securement device from FIG. 18A with release liners attached.

FIG. 18B shows the securement device 180 with two removeable release liners 40c and 40d attached. The release liner 40c covers the gel pad 30c and the surface of the body member 20c to which the gel pad 30c is attached. The release liner 40d covers adhesive portions on a surface of the body member 20c opposite the surface to which the gel pad 30c is attached. In other embodiments, several release liners may be attached to one or both of the surfaces of the securement device 180. In some embodiments, the release liner 40c may be smaller so as to be substantially coextensive with the gel pad 30c. In some embodiments, one or more of the release liners 40c and 40d are omitted. In the illustrated embodiment, the release liners 40c and 40d are configured to have a shape that roughly corresponds to the shape of the body member 20c, but in some embodiments the release liner 40c and/or 40d may be sized or shaped differently. The release liners 40c and 40d may otherwise be configured similar to the release liner 40a, illustrated in FIG. 1B.

Figure 19:
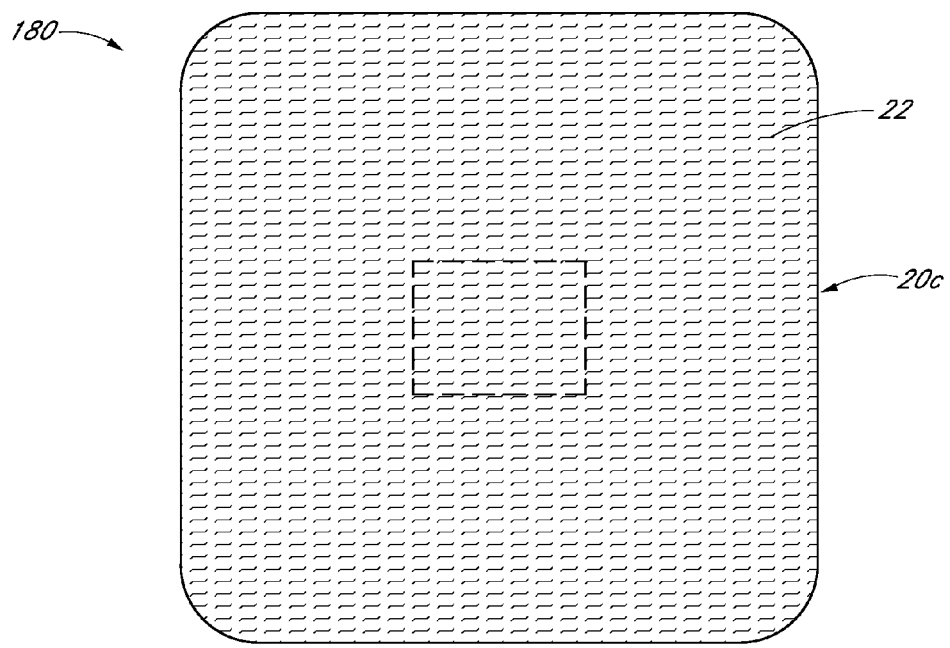
FIG. 19 is a bottom view of the securement device from FIG. 18A.

The bottom surface 22 of the body member 20c, shown in a bottom view of the securement device 180 in FIG. 19, comprises an adhesive. As described above in reference to the securement device 10 and the body member 20a, the body member 20c may be configured as an adhesive dressing, or an adhesive may be coated onto the bottom surface 22. In the illustrated embodiment, the adhesive is formed over the extent of the bottom surface 22. In other embodiments, the adhesive may only partially cover the bottom surface 22, and may be formed in various patterns and shapes. The adhesive comprises a compound configured to adhere to the skin of a patient, as described above.

Figure 20:
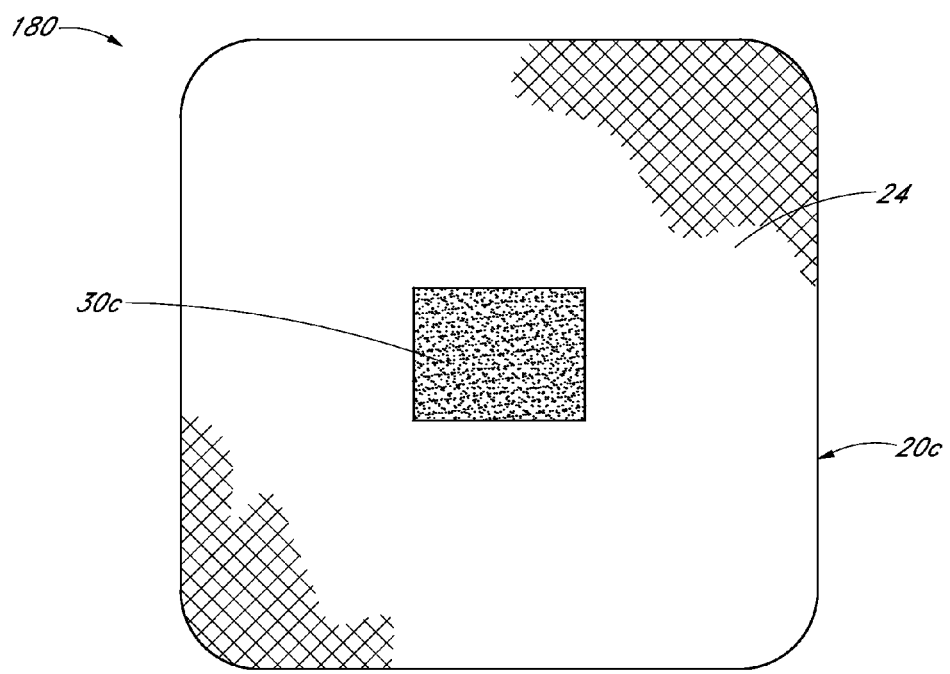
FIG. 20 is a top view of the securement device from FIG. 18A.

As can be seen in a top view of the securement device 180 in FIG. 20, the gel pad 30c is attached to the top surface 24 of the body member 20c. In the illustrated embodiment, the gel pad 30c is approximately centered on the body member 20c. In other embodiments, the gel pad 30c may be off-centered. In some embodiments, a plurality of gel pads may be attached to the top surface 24. The plurality of gel pads may be configured to secure one or more medical articles. The top surface 24 forms a mounting surface for attachment of other securement devices, as described in more detail below. In some embodiments, a portion of the top surface 24 comprises an adhesive.

Figure 21:
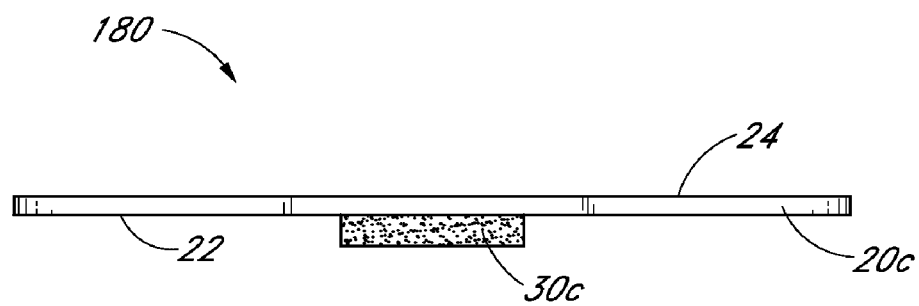
FIG. 21 is a side view of the securement device from FIG. 18A.
Figure 22:
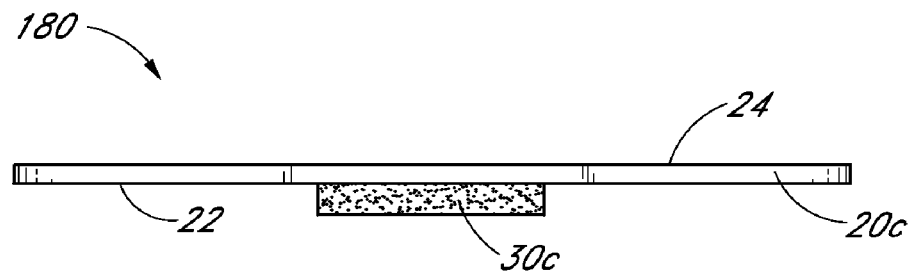
FIG. 22 is a front view of the securement device from FIG. 18A.

As can be seen in a side view of the securement device 180 in FIG. 21 and a front view of the securement device 180 in FIG. 22, the body member 20c is illustrated as being approximately square. In other embodiments, the body member 20c may be configured in other shapes. The illustrated square shape, however, may be advantageous when attaching other securement devices, as described in more detail below. The body member 20c may otherwise be configured similar to the body member 20a, illustrated in FIG. 1A.

Figure 23:
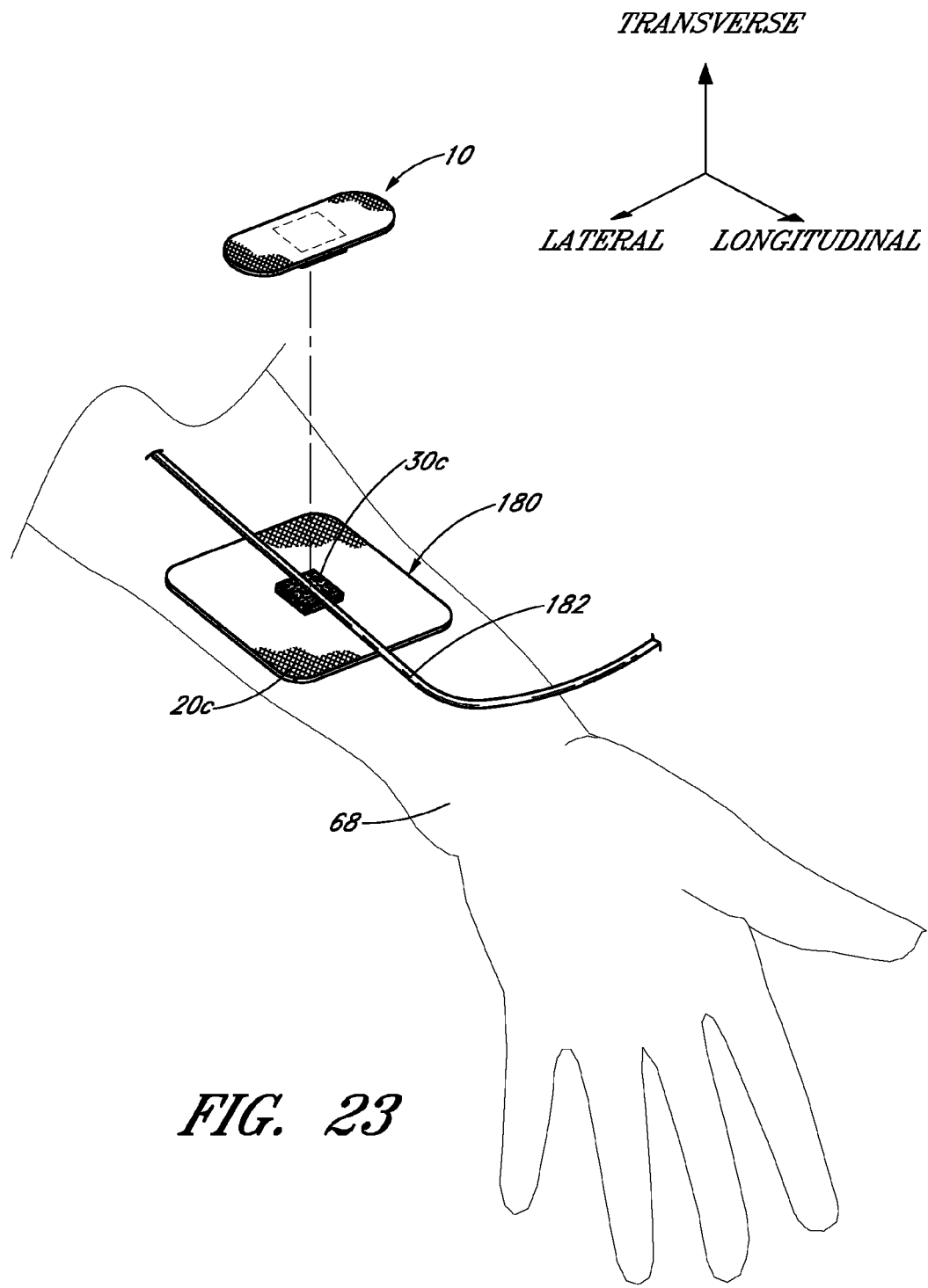
FIG. 23 is a perspective view of a securement system in accordance with an embodiment of the present invention and shows the securement device from FIG. 18A attached to a patient's skin, a medical article placed on the securement device from FIG. 18A, and the securement device from FIG. 1A positioned above the medical article.
Figure 24:
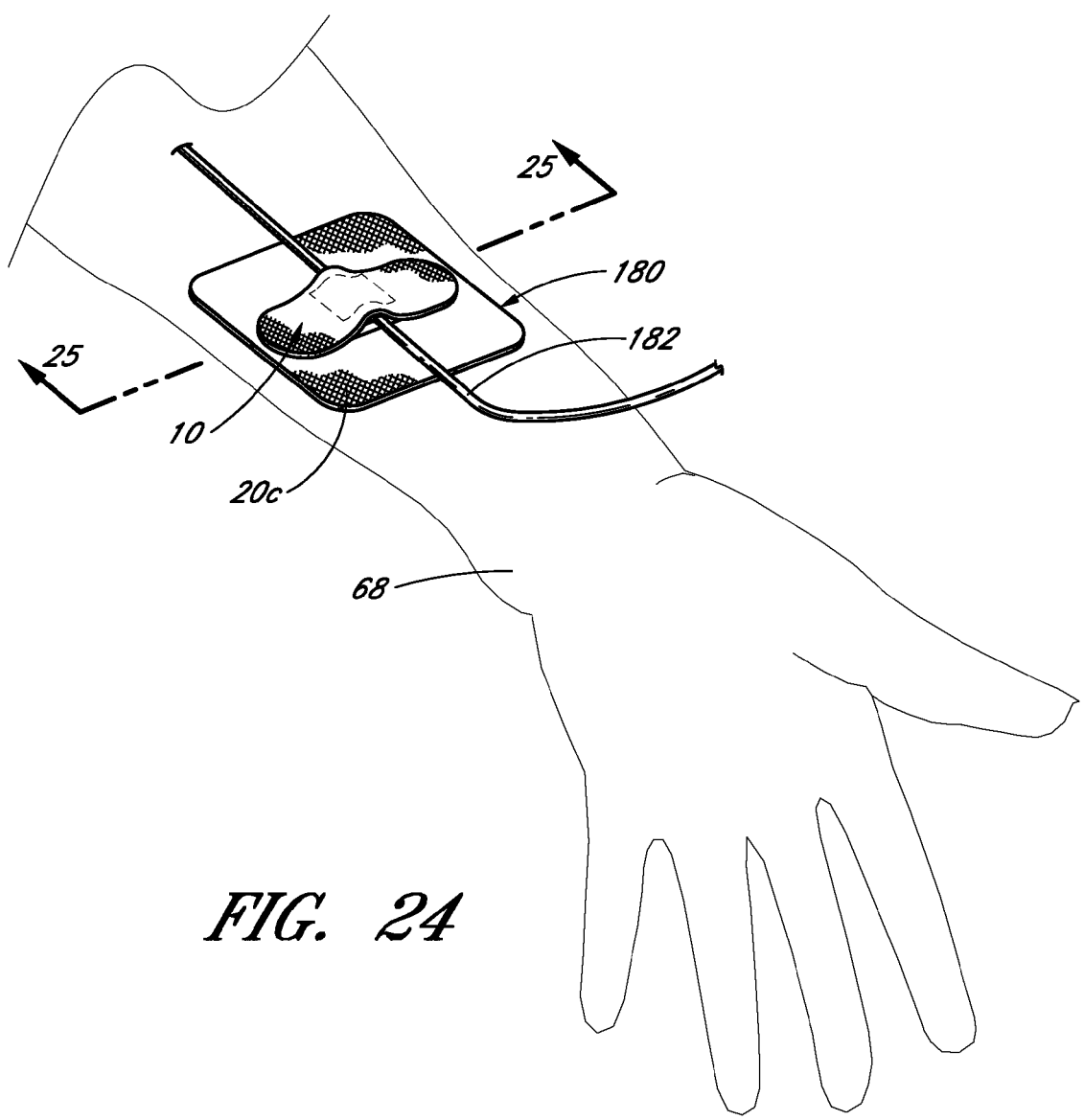
FIG. 24 is a perspective view of the securement system from FIG. 23 secured about the medical article.

A medical article can be secured to a patient by using the securement device 180 and another securement device, as shown in FIGS. 23 and 24. In the illustrated embodiment, the medical article 182 includes a lumen configured to transport liquids, and the other securement device is the securement device 10 illustrated in FIG. 1A.

In FIG. 23, the securement device 180 is adhered to the patient's arm 68. After placing the medical article 182 above the securement device 180, a medical provider can then lower the medical article 182 onto the securement device 180 such that the medical article 182 is in contact with the gel pad 30c. Then, the securement device 10 may be lowered over the medial article 182 and pressed against the securement device 180 to attach the securement device 10 to the securement device 180 and secure the medical article 182. The medical article 182 will thus be held on the patient, as shown in FIG. 24. Of course, the medical provider may first attach the medical article 182 to the securement device 10 and then attach the combination of the securement device 10 and the medical article 182 to the securement device 180 in embodiments where the gel pad of the securement device 10 is configured to self-adhere to the medical article 182.

As described above, the top surface 24, see FIG. 20, forms a mounting surface. The mounting surface is configured such that a securement device may be attached to thereto. In the illustrated embodiment, the mounting surface is free of adhesives, and comprises a surface on which a securement device may be adhered. The mounting surface may be smooth, glossy, or textured, or otherwise configured such that a securement device may be adhered thereto. In other embodiments, the mounting surface may comprise an adhesive to attach to a securement device placed thereon.

The mounting surface may be configured such that an attached securement device may be detached or removed. For example, the mounting surface may be configured as a smooth surface from which the securement device 10 may be peeled without damaging the securement device 180. In some embodiments, a securement device that has been removed from the mounting surface may be reattached. Those skilled in the art will appreciate that repeated removal and reattachment of securement devices and/or medical articles to the mounting surface will not cause discomfort to the patient, and that the mounting surface shield the patient's skin from excoriation. Of course, in some embodiments the mounting surface and/or an adhesive or other attachment feature of an attaching securement device may be configured to permanently attach to the mounting surface.

The mounting surface is not limited to attaching or coupling with a securement device using adhesives. For example, the mounting surface may comprise hook and/or loop fasteners configured to engage a securement device. In one embodiment, the mounting surface has snap fasteners configured to engage snap fasteners on a securement device. In some embodiments, a portion of a securement device may be permanently or semi-permanently attached to the mounting surface such that another portion of the securement device can be rotated, folded, or bent over a medical article and secured to the mounting surface.

In the illustrated embodiment, the body member 20c is configured such that the securement device 10 can be secured over the gel pad 30c in any configuration or rotation. In other embodiments, the body member 20c is configured in another size or shape that also allows securement of the securement device 10 over the gel pad 30c in any configuration or rotation. For example, the body member 20c may be configured in the shape of a circle. In some embodiments, the size and/or shape of the body member 20c may be more closely matched with the size and/or shape of the securement device 10. In such embodiment, there may be a limited number of configurations for attaching the securement device 10 to the mounting surface and over the gel pad 30c.

Figure 25:
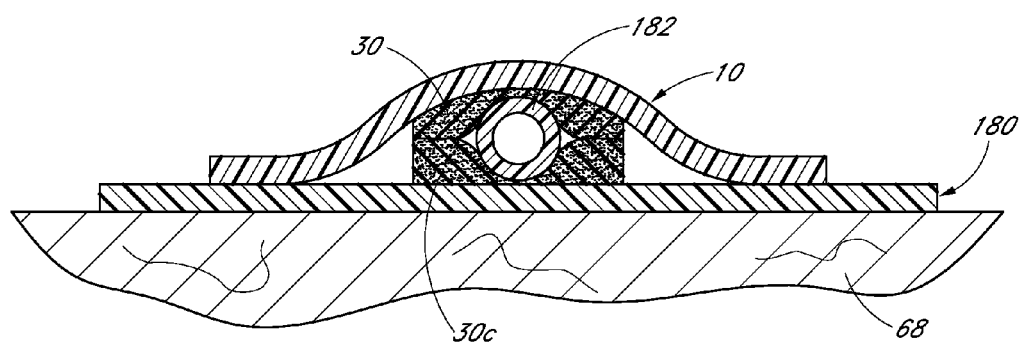
FIG. 25 is a cross-section view taken along line 25-25 of FIG. 24 and shows two gel pads deformed about the medical article.

As can be seen in a cross-section view taken along line 25-25 of FIG. 24, which cross-section view is illustrated in FIG. 25, both the gel pad 30 of the securement device 10 and the gel pad 30c of the securement device 180 may conform to the shape of an outer surface of the lumen 182. In this way, the gel pad 30 and the gel pad 30c may in combination at least partially encase the medical article 182 without substantially occluding the lumen. Securing the medical article 182 in this configuration inhibits motion. For example, lateral, longitudinal, transverse, and/or rotational movement of the medical article 182 may be inhibited in this configuration.

Those skilled in the art will recognize that although the securement device 180 is illustrated in combination with the securement device 10 in FIG. 25, other securement devices besides the securement device 10 may be used in combination with the securement device 180 or portions thereof.

Figure 26:
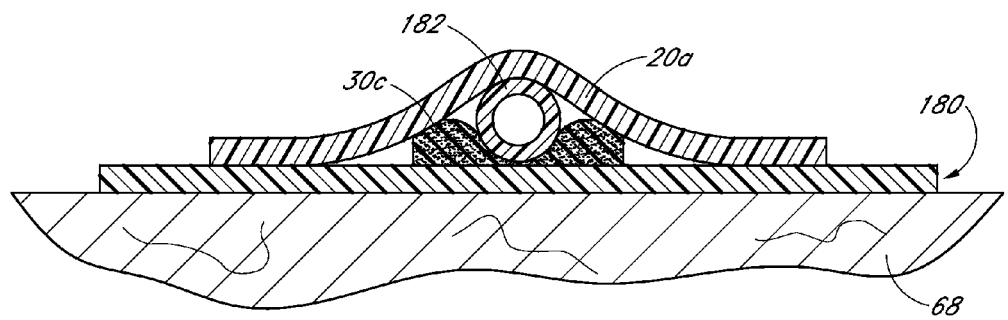
FIG. 26 is a cross-section view similar to FIG. 25 except that the securement device from FIG. 1A does not include its own gel pad.

FIG. 26 illustrates a cross-section view of another combination, in which the gel pad 30 is omitted from the securement device 10 such that only the body member 20a remains. In this embodiment, the body member 20a is placed over the medical article 182 and adhered to the securement device 180 such that the gel pad 30c, which is attached to the securement device 180, is deformed about the medical article 182. In other embodiments, medical tape may be placed over the medical article 182 and adhered to the securement device 180 in a similar fashion.

Figure 27:
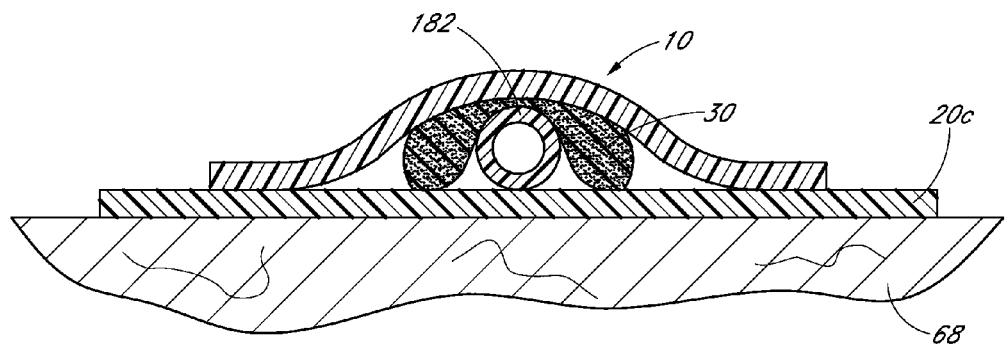
FIG. 27 is a cross-section view similar to FIG. 25 except that the securement device from FIG. 18A does not include its own gel pad.

FIG. 27 illustrates a cross-section view of yet another combination, in which the gel pad 30 is omitted from the securement device 180 such that only the body member 20c remains. In this embodiment, the securement device 10 is placed over the medical article 182 and adhered to the body member 20c such that the gel pad 30, which is attached to the securement device 10, is deformed about the medical article 182. In one such embodiment, the body member 20c comprises an anchor pad configured for attachment to the patient's skin.

Although the securement device 180 is illustrated as securing a medical article 182 having a tubular shape, the securement device 180 can be used to secure a variety of medical articles, singularly or in combination, in position upon a patient. The securement device 180 and/or another securement device used in combination with the securement device 180 may comprise one or more gel pads. For example, the securement device 180 may be used in combination with the securement device 100. When using the securement device 100 with the securement device 180, the securement device 100 can be adhered to the securement device 180 over a medical article such that the gel pad 30c approximately aligns with the intermediate portion 29 of the securement device 100. In some embodiments, the gel pad 30c is configured to self-adhere to a medical article such that a medical article can be secured to the securement device 180 without the need for another securement device. The securement device 180 may be packaged in a kit including one or more other securement devices.

Figure 28A:
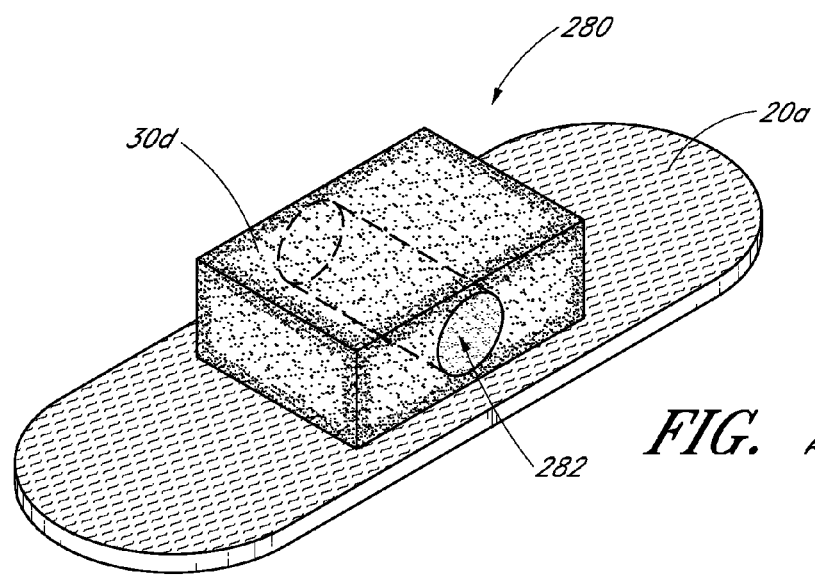
FIG. 28A is a perspective view of a securement device in accordance with another embodiment of the present invention and shows a gel or foam pad with a hole formed therethrough.

With reference now to FIG. 28A, an embodiment of a securement device 280 includes the body member 20a and a gel pad 30d. The gel pad 30d is attached to the body member 20a. The gel pad 30d is configured similar to the gel pad 30, illustrated in FIG. 1A, with the exceptions of the gel pad 30d being thicker and formed with a channel 282 therethrough. For ease of illustration, the securement device 280 is shown upside down in FIG. 28A. Thus, the gel pad 30d is actually attached to a bottom surface of the body member 20a.

Figure 28B:
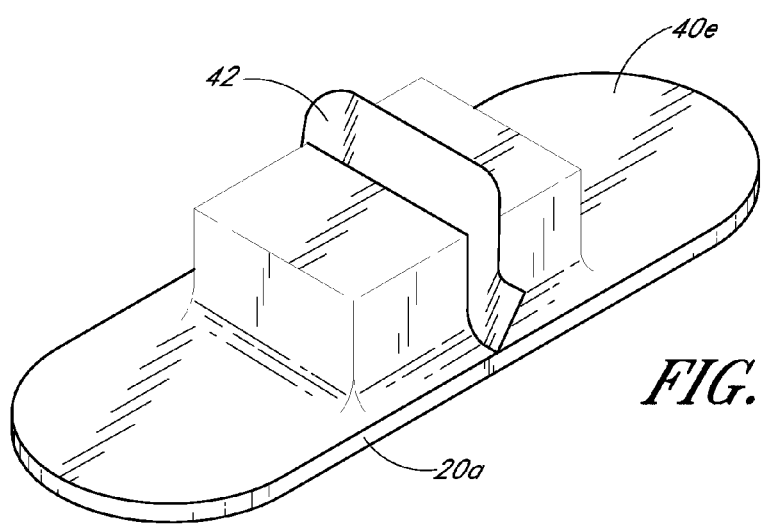
FIG. 28B is a perspective view of the securement device from FIG. 28A with a release liner attached.

FIG. 28B shows the securement device 280 with a removeable release liner 40e attached. The release liner 40e covers the gel pad 30d and adhesive portions of the body member 20a. The release liner 40e is longer than the release liner 40a illustrated in FIG. 1B to accommodate the increased thickness of the gel pad 30d, but may otherwise be configured similar to the release liner 40a.

Figure 29:
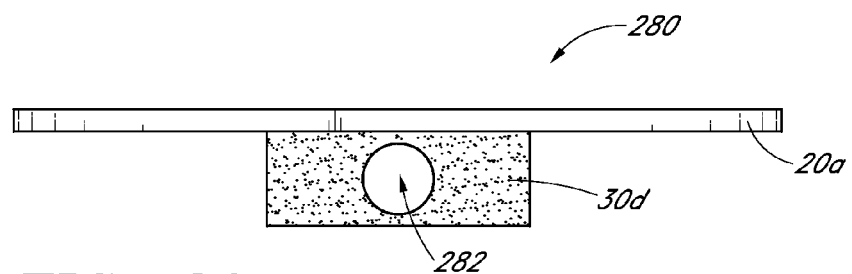
FIG. 29 is a front view of the securement device from FIG. 28A.

As can be seen in a front view of the securement device 280 in FIG. 29, the channel 282 is illustrated as having a circular cross-sectional shape and extends along the longitudinal axis. In the illustrated embodiment, the channel 282 is configured to accept a tubular medical article, but in other embodiments the channel 282 has any number of shapes and sizes. In addition, the shape or size of a cross-section of the channel may vary along the length of the channel. Additionally, the channel may be formed in a shape which does not follow the longitudinal axis. For example, a curved channel may aid in proper placement of a medical article or may keep the medical article in a configuration that will not interfere with a medical practitioner aiding a patient to which the securement device 280 is attached. A plurality of the gel pads 30d may be attached to the body member 20a, or a combination of gel pads with channels and gel pads without channels may be attached to the body member 20a.

Figure 30:
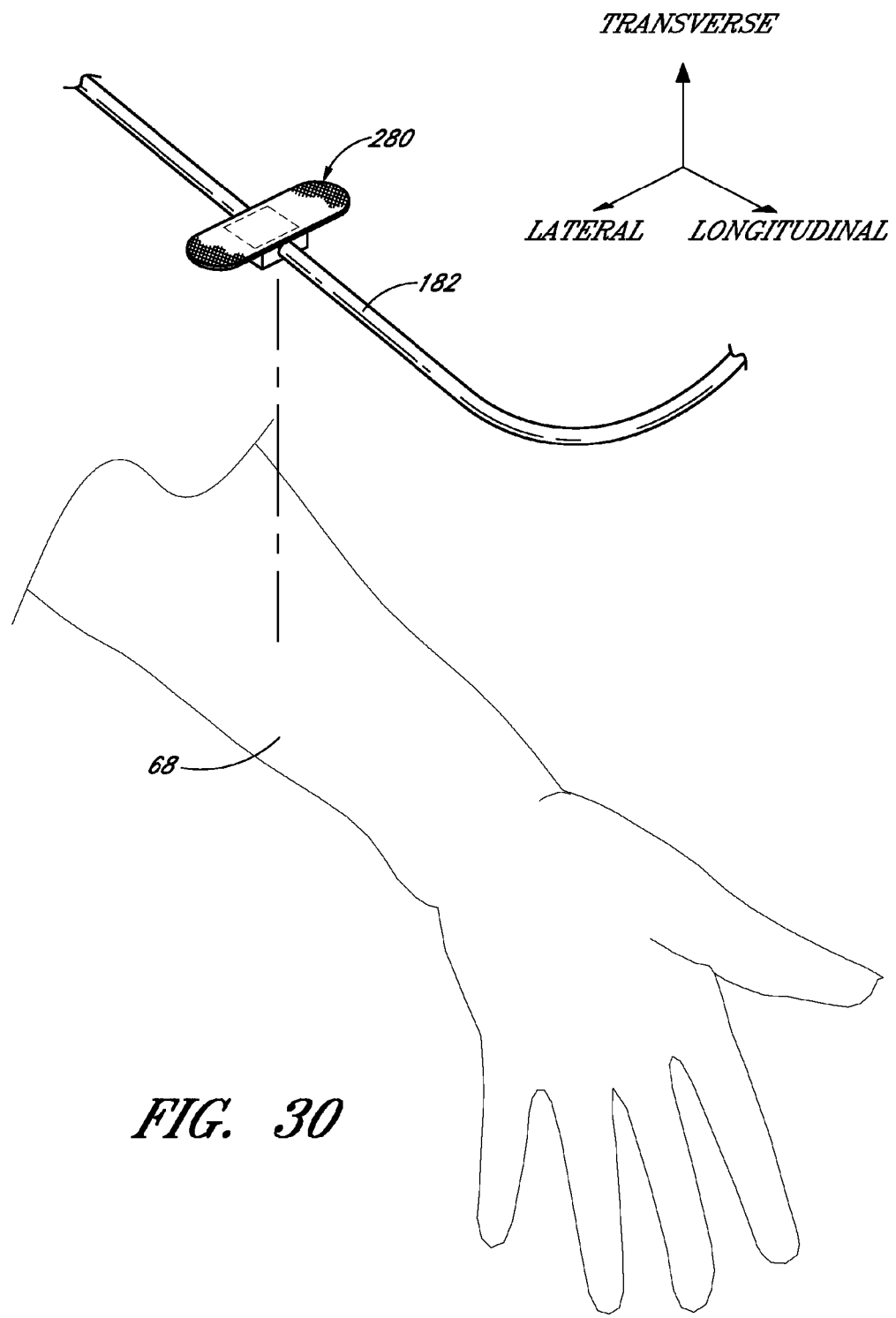
FIG. 30 is a perspective view of the securement device from FIG. 28A and a medical article positioned above a patient's skin.
Figures 31, 32:
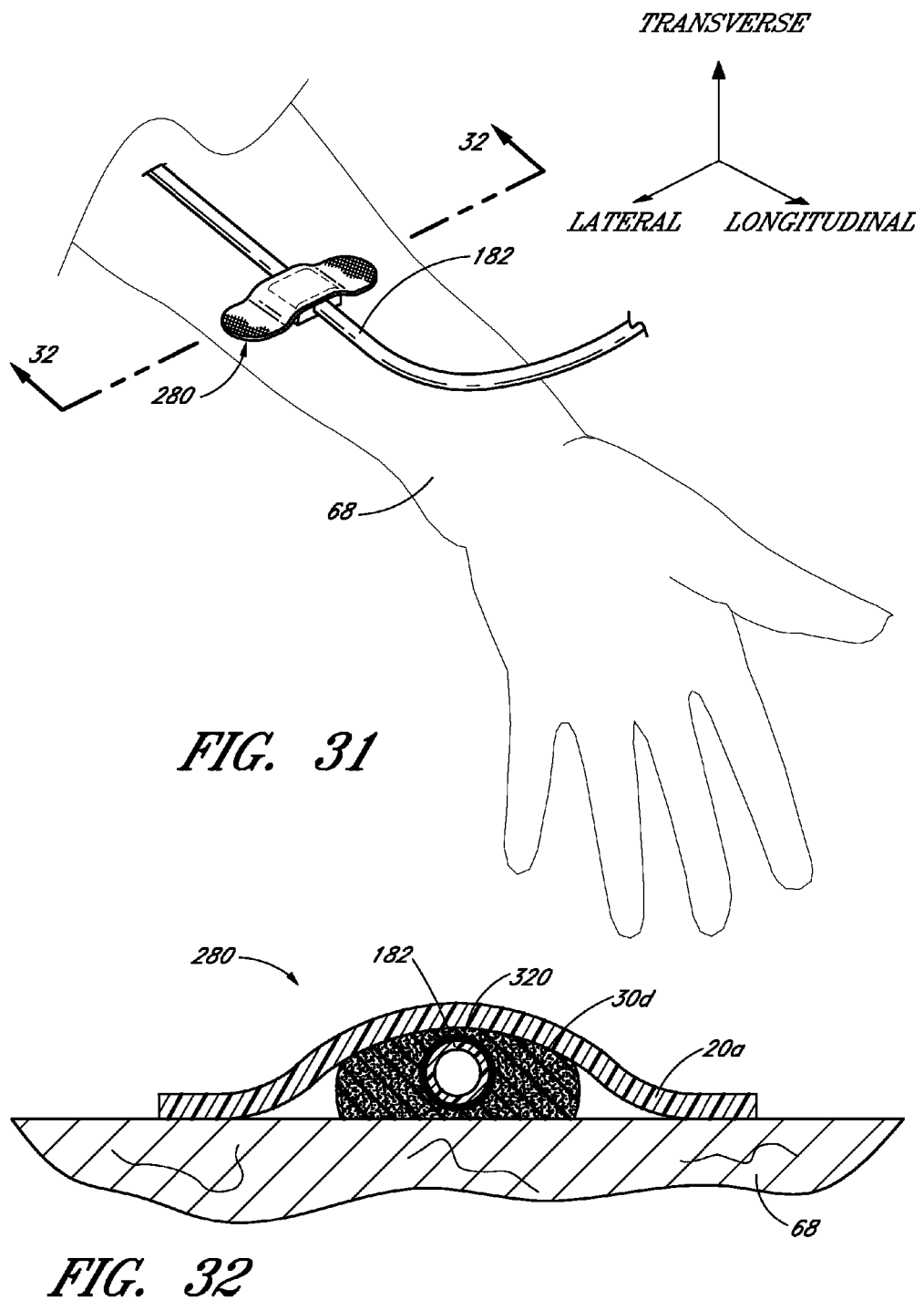
FIG. 31 is a perspective view of the securement device from FIG. 28A and the medical article attached to the patient.
FIG. 32 is a cross-section view taken along line 32-32 of FIG. 31 and shows a space between the medical article and the gel or foam pad filled in with a gel or foam.

A medical article can be secured to a patient by the securement device 280, as shown in FIGS. 30 and 31. In the embodiment shown in FIG. 30, the securement device 280 is illustrated as being placed above the patient's arm 68 with the medical article 182 passing through the channel 282. A medical provider can lower the securement device 280 onto the patient's arm 68 and press the securement device 280 against the patient such that the gel pad 30d presses against the medical article 182 and such that the adhesive on the body member 20a adheres to the skin of the patient's arm 68. The medical article 182 will thus be held on the patient by the securement device 280, as shown in FIG. 31.

As can be seen in a cross-section view taken along line 32-32 of FIG. 31, which cross-section view is illustrated in FIG. 32, the gel pad 30d conforms to the shape of an outer surface of the medical article 182. As a result, a variety of medical articles of varying diameter may be accepted within the channel 282 and secured by the securement device 280. Such secured medical articles will be inhibited from moving in at least a transverse direction, and may further be inhibited from moving in a lateral and/or longitudinal direction.

In the illustrated embodiment, the area between the gel pad 30d and the medical article 182 is filled in with a spray material 320. The spray material may comprise spray foam or gel, such as spray memory foam or a spray-in-the-can alginate. The securement device 280 may be packaged in the form of a kit including the spray foam or gel. Of course, the spray material 320 may be omitted when securing a medical article using the securement device 280. A gel material may be used to fill in an area between any of the gel pads 30, 30a, 30b, and 30c and a patient's skin, and/or to fill in an area between any of the gel pads 30, 30a, 30b, and 30c and another gel pad or surface. The securement devices 10, 100, and 180 may similarly be packaged with a spray foam or gel.

Various aspects are described above with reference to specific forms or embodiments selected for purposes of illustration. It will be appreciated that the spirit and scope of the disclosed securement system is not limited to the selected forms. Moreover, it is to be noted that the figures provided are not drawn to any particular proportion or scale, and that many variations can be made to the illustrated embodiments. Thus, although the system has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations have been shown and described in detail, other modifications, which are within the scope of this invention, will be readily apparent to those of skill in the art based upon this disclosure.

It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure and the claims that follow.

Although the above embodiments and devices, systems, and methods have been described in terms of use in medical device applications, those skilled in relevant arts will recognize that such embodiments, devices, systems, and methods can be employed with any suitable non-medical applications and in some instances may be configured for use with animals.

All patents, test procedures, and other documents cited herein, including priority documents, are fully incorporated by reference to the extent such disclosure is not inconsistent with this invention and for all jurisdictions in which such incorporation is permitted.

What is claimed is:

1. A securement device for a medical device, comprising:
a body having a top surface and a bottom surface, said bottom surface having an adhesive compound thereon; and
a resilient retainer formed from a soft, tacky elastomeric gel or an elastomeric foam and being supported by said body, said resilient retainer having a channel extending along a longitudinal axis, said channel being adapted for receiving and securing a medical device, the medical device being secured to the skin of a patient upon affixing said bottom surface to the patient via said adhesive compound, wherein said elastomeric gel is formed by curing an organopolysiloxane composition.

2. The securement device of claim 1, wherein said medical device is a catheter.

3. The securement device of claim 1, wherein said channel is preformed into a desired shape for receiving and securing the medical device.

4. The securement device of claim 3, wherein a space between said channel and the medical device is filled with a gel or foam.

5. The securement device of claim 4, wherein said gel or foam comprises spray gel or foam.

6. The securement device of claim 1, wherein said organopolysiloxane composition comprises:
a vinyl-containing high viscosity organopolysiloxane or a blend of high viscosity vinyl-containing organopolysiloxanes;
a low viscosity organopolysiloxane or a blend of low viscosity organopolysiloxanes;
a reinforcing filler;
a platinum catalyst; and
a hydrogen containing polysiloxane copolymer,
wherein a molar ratio of hydrogen to vinyl radicals in the total composition is less than 1.2, such that after curing, the degree to which said tacky, reinforced polysiloxane elastomer is partially crosslinked is about 30 to about 90%.

7. The securement device of claim 6, wherein the organopolysiloxane composition has a hardness of about 5 to about 55 durometer units (Shore 00), a tackiness of about 0 to about 450 grams as determined by a polyken probe tack tester or about 0 to about 7.6 cm as determined by a rolling ball tack tester and a tensile strength of about 0.14 to about 5.52 mega Pascals, a minimum elongation of about 250 to about 1100 percent and a tear strength of about 0.8 to about 35.2 kN/m.

8. The securement device of claim 1, wherein the organopolysiloxane composition comprises, based upon 100 parts total composition:
20 to 90 parts of a vinyl-containing high viscosity organopolysiloxane or a blend of high viscosity vinyl-containing organopolysiloxanes having no more than 25 mole percent of phenyl radicals and having a viscosity of 2,000 to 1,000,000 centipoise at 25° C. of the formula:

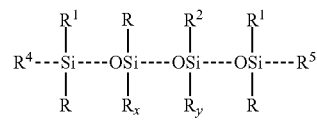

where $R^1$ is selected from the class consisting of alkenyl, alkyl and aryl radicals and R is a monovalent hydrocarbon radical, $R^2$ is selected from the class consisting of alkyl and aryl radicals, $R^4$ and $R^5$ are independently selected from the class consisting of alkyl and vinyl radicals; x varies from zero to 3000; and y varies from 0 to 300;
from 5 to 40 parts of a polymer selected from the class consisting of a low viscosity organopolysiloxane and a blend of low viscosity organopolysiloxanes having viscosity that varies from 20 to 5,000 centipoise at 25° C. and having no more than 25 mole percent phenyl radicals of the formula

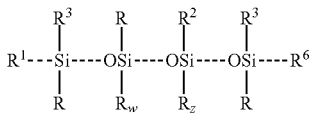

wherein $R^1$ and $R^6$ are independently selected from the class consisting of alkenyl, alkyl and aryl radicals, $R^2$ and R are as previously defined, $R^3$ is selected from the class consisting of alkyl, aryl and alkenyl radicals, w varies from 0 to 500, and z varies from 0 to 200;

from 10 to 70 parts of a reinforcing filler;

from 0.1 to 50 parts per million of platinum catalyst (as platinum metal) to the total composition; and from 0.1 to 50 parts of a hydrogen containing polysiloxane copolymer, wherein the molar ratio of hydrogen to alkenyl radicals in the total uncured composition is less than 1.2, such that after curing, the degree to which the soft, tacky, reinforced polysiloxane elastomer is partially crosslinked is about 30 to about 90%.

9. The securement device of claim 1, wherein said elastomeric foam is a memory foam comprising polyurethane.

10. A method of securing a medical device to a patient, comprising:

providing a securement device for the medical device, and including a body having a top surface and a bottom surface, the bottom surface having an adhesive compound thereon, and a retainer formed from a soft, tacky elastomeric gel or an elastomeric foam, the retainer being supported by the bottom surface of the body and having a channel extending along a longitudinal axis, said channel being adapted for receiving a medical device, wherein the elastomeric gel is formed by curing an organopolysiloxane composition;

locating the medical device on the resilient retainer; and securing the securement device and medical device to the patient with the body via the adhesive compound.

11. The method of claim 10, wherein the medical device is a catheter.

12. The method of claim 10, wherein the channel has a size and shape to receive at least a portion of the medical device.

13. The method of claim 12 further comprising filling a space between the channel and the medical device with a gel or foam.

14. The method of claim 13, wherein the gel or foam comprises spray gel or foam.

15. The method of claim 10, wherein said organopolysiloxane composition comprises:

a vinyl-containing high viscosity organopolysiloxane or a blend of high viscosity vinyl-containing organopolysiloxanes;

a low viscosity organopolysiloxane or a blend of low viscosity organopolysiloxanes;

a reinforcing filler;

a platinum catalyst; and a hydrogen containing polysiloxane copolymer, wherein a molar ratio of hydrogen to vinyl radicals in the total composition is less than 1.2, such that after curing, the degree to which said tacky, reinforced polysiloxane elastomer is partially crosslinked is about 30 to about 90%.

16. The method of claim 15, wherein the organopolysiloxane composition has a hardness of about 5 to about 55 durometer units (Shore 00), a tackiness of about 0 to about 450 grams as determined by a polyken probe tack tester or about 0 to about 7.6 cm as determined by a rolling ball tack tester and a tensile strength of about 0.14 to about 5.52 mega Pascals, a minimum elongation of about 250 to about 1100 percent and a tear strength of about 0.8 to about 35.2 kN/m.

17. The method of claim 10, wherein the organopolysiloxane composition comprises, based upon 100 parts total composition:

20 to 90 parts of a vinyl-containing high viscosity organopolysiloxane or a blend of high viscosity vinyl-containing organopolysiloxanes having no more than 25 mole percent of phenyl radicals and having a viscosity of 2,000 to 1,000,000 centipoise at 25° C. of the formula:

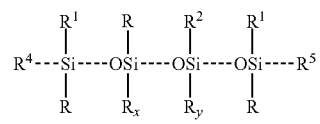

where $R^1$ is selected from the class consisting of alkenyl, alkyl and aryl radicals and R is a monovalent hydrocarbon radical, $R^2$ is selected from the class consisting of alkyl and aryl radicals, $R^4$ and $R^5$ are independently selected from the class consisting of alkyl and vinyl radicals; x varies from zero to 3000; and y varies from 0 to 300;

from 5 to 40 parts of a polymer selected from the class consisting of a low viscosity organopolysiloxane and a blend of low viscosity organopolysiloxanes having viscosity that varies from 20 to 5,000 centipoise at 25° C. and having no more than 25 mole percent phenyl radicals of the formula

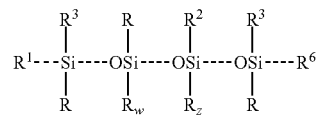

wherein $R^1$ and $R^6$ are independently selected from the class consisting of alkenyl, alkyl and aryl radicals, $R^2$ and R are as previously defined, $R^3$ is selected from the class consisting of alkyl, aryl and alkenyl radicals, w varies from 0 to 500, and z varies from 0 to 200;

from 10 to 70 parts of a reinforcing filler;

from 0.1 to 50 parts per million of platinum catalyst (as platinum metal) to the total composition; and from 0.1 to 50 parts of a hydrogen containing polysiloxane copolymer, wherein the molar ratio of hydrogen to alkenyl radicals in the total uncured composition is less than 1.2, such that after curing, the degree to which the soft, tacky, reinforced polysiloxane elastomer is partially crosslinked is about 30 to about 90%.

18. The method of claim 10, wherein said elastomeric foam is a memory foam comprising polyurethane.

19. A securement system, comprising:
a flexible body member having a first surface and a second surface located opposite the first surface, the first surface comprising an adhesive configured for attachment to a patient; and
a tacky gel pad supported by the flexible body member and configured to form a channel extending along a longitudinal axis when pressed against a medical article, the gel pad inhibiting at least lateral and longitudinal motion of the medical article when the flexible body member is attached to the patient, wherein said gel pad is formed by curing an organopolysiloxane composition.

20. The securement system of claim 19, comprising a plurality of tacky gel pads configured to deform when pressed against the medical article.

21. The securement system of claim 19 further comprising an anchor pad having a top surface and a bottom surface, the top surface comprising a mounting surface configured for attachment to the flexible body member, the bottom surface comprising an adhesive configured for attachment to the patient's skin.

22. The securement system of claim 21, comprising a plurality of flexible body members and a plurality of gel pads, wherein the mounting surface is configured for attachment to the plurality of flexible body members.

23. The securement system of claim 21, wherein the flexible body member is releasably attached to the mounting surface.

24. The securement system of claim 19, wherein the tacky gel pad is attached to the first surface of the flexible body member.

25. The securement system of claim 19, wherein the tacky gel pad is attached to the second surface of the flexible body member.

26. A securement device for a medical device, comprising:
a body having a top surface and a bottom surface, said bottom surface having an adhesive compound thereon; and
a resilient retainer formed from a soft, tacky elastomeric gel or an elastomeric foam and being supported by said body, said resilient retainer having a channel extending along a longitudinal axis, said channel being adapted for receiving and securing a medical device, the medical device being secured to the skin of a patient upon affixing said bottom surface to the patient via said adhesive compound, wherein said elastomeric foam is a memory foam comprising polyurethane.

27. A method of securing a medical device to a patient, comprising:
providing a securement device for the medical device, and including a body having a top surface and a bottom surface, the bottom surface having an adhesive compound thereon, and a retainer formed from a soft, tacky elastomeric gel or an elastomeric foam, the retainer being supported by the bottom surface of the body and having a channel extending along a longitudinal axis, said channel being adapted for receiving a medical device, wherein said elastomeric foam is a memory foam comprising polyurethane;
locating the medical device on the resilient retainer; and
securing the securement device and medical device to the patient with the body via the adhesive compound.

* * * * *